United States Patent
Colarusso et al.

(10) Patent No.: US 7,795,250 B2
(45) Date of Patent: Sep. 14, 2010

(54) INDOLE DERIVATIVES AS ANTIVIRAL AGENTS

(75) Inventors: Stefania Colarusso, Rome (IT); Immacolata Conte, Rome (IT); Joerg Habermann, Rome (IT); Frank Narjes, Rome (IT); Simona Ponzi, Rome (IT)

(73) Assignee: Istituto di Ricerche di Biologia Molecolare P Angeletti SpA, Pomezia, Rome (IT)

( * ) Notice: Subject to any disclaimer, the term of this patent is extended or adjusted under 35 U.S.C. 154(b) by 359 days.

(21) Appl. No.: 11/628,905

(22) PCT Filed: Jun. 8, 2005

(86) PCT No.: PCT/EP2005/052631
§ 371 (c)(1),
(2), (4) Date: Jan. 14, 2008

(87) PCT Pub. No.: WO2004/087714
PCT Pub. Date: Oct. 14, 2004

(65) Prior Publication Data
US 2008/0261944 A1    Oct. 23, 2008

(30) Foreign Application Priority Data
Jun. 11, 2004    (GB) .................... 0413087.8

(51) Int. Cl.
| | |
|---|---|
| *A61K 31/4045* | (2006.01) |
| *A61K 31/5355* | (2006.01) |
| *A61K 31/4184* | (2006.01) |
| *A61K 31/454* | (2006.01) |
| *A61K 31/496* | (2006.01) |
| *A61K 31/541* | (2006.01) |
| *A61K 31/4406* | (2006.01) |
| *C07D 209/12* | (2006.01) |
| *C07D 413/12* | (2006.01) |
| *C07D 235/08* | (2006.01) |
| *C07D 401/12* | (2006.01) |
| *C07D 409/12* | (2006.01) |
| *C07D 403/12* | (2006.01) |
| *C07D 279/12* | (2006.01) |

(52) U.S. Cl. ............ 514/228.2; 514/235.2; 514/254.09; 514/323; 514/339; 514/394; 514/414; 514/419; 544/58.2; 544/143; 544/373; 546/201; 546/277.4; 548/305.1; 548/454; 548/455; 548/468; 548/496

(58) Field of Classification Search .................. None
See application file for complete search history.

(56) References Cited
FOREIGN PATENT DOCUMENTS

| | | | |
|---|---|---|---|
| WO | WO 03/010140 A2 | | 2/2003 |
| WO | WO 03/010141 A2 | | 2/2003 |
| WO | WO 2004/065367 | * | 1/2004 |
| WO | WO 2004/035571 A1 | | 4/2004 |
| WO | WO 2004/065367 | * | 8/2004 |
| WO | WO 2004/065367 A1 | | 8/2004 |
| WO | WO 2004/087714 A1 | | 10/2004 |

* cited by examiner

*Primary Examiner*—Golam M. M. Shameem
*Assistant Examiner*—Alicia L Fierro
(74) *Attorney, Agent, or Firm*—Sheldon O. Heber; Julie M. Lake; Kenneth R. Walton

(57) ABSTRACT

The present invention relates to indole compounds of the formula (I): wherein $R^1$, $R^2$, $R^3$, $R^4$, A, E and X are as defined herein, and pharmaceutically acceptable salts thereof, useful in the prevention and treatment of hepatitis C infections.

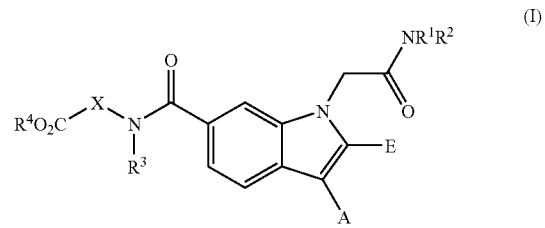

(I)

9 Claims, No Drawings

INDOLE DERIVATIVES AS ANTIVIRAL AGENTS

This application is the National Stage of International Application No. PCT/EP2005/052631, filed on Jun. 8, 2005, which claims the benefit of United Kingdom Application No. 0413087.8, filed Jun. 11, 2004.

The present invention relates to indole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit. Published International patent applications WO 03/010140 and WO 03/010141 (Boehringer Ingelheim) suggest indole derivatives as possible inhibitors of HCV polymerase and illustrate thousands of possible compounds. However, neither patent application describes or suggests an indole in which the indole nitrogen is substituted by an alkylamide residue.

The present invention provides compounds of the formula (I):

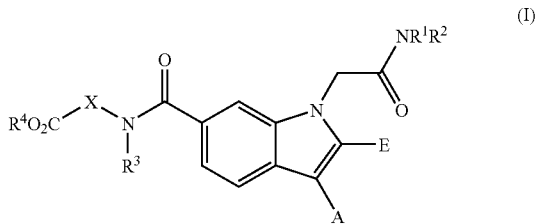

wherein:

E is hydrogen, $C_{1-6}$alkyl, $C_{2-6}$alkenyl, $C_{2-6}$alkynyl, $C_{3-8}$cycloalkyl or a moiety containing at least one aromatic ring and possesses 5-, 6-, 9- or 10-ring atoms optionally containing 1, 2 or 3 heteroatoms independently selected from N, O and S, which ring is optionally substituted at any substitutable position by groups $Q^1$ and $Q^2$;

$Q^1$ is halogen, hydroxy, $C_{1-4}$alkyl, $C_{1-4}$alkoxy, aryl, heteroaryl, $CONR^aR^b$, $C_nH_{2n}NR^aR^b$, —O—$(CH_2)_{2-4}R^aR^b$, —O—$C_nH_{2n}CONR^aR^b$, —O—$C_nH_{2n}$aryl, —O—$C_nH_{2n}$heteroaryl, —O—$CHR^cR^d$;

$R^a$ and $R^b$ are each independently selected from hydrogen, $C_{1-4}$alkyl and $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

n is 0, 1, 2 or 3

$R^c$ and $R^d$ are each independently selected from, hydrogen and $C_{1-4}$alkoxy;

or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is $C_{1-6}$alkyl, $C_{2-6}$alkenyl, where said $C_{1-6}$alkyl and $C_{2-6}$alkenyl groups are optionally substituted by $C_{1-4}$alkoxy or up to 5 fluorine atoms, or a non-aromatic ring of 3 to 8 ring atoms where said ring may contain a double bond and/or may contain a O, S, SO, $SO_2$ or NH moiety and where said ring is optionally substituted by one or two alkyl groups of up to 2 carbon atoms or by 1 to 8 fluorine atoms, or a non-aromatic bicyclic moiety of 4 to 8 ring atoms which ring may be optionally substituted by fluorine or hydroxy;

$R^1$ and $R^2$ are each independently selected from hydrogen, $C_{1-6}$alkyl, $C_{2-6}$alkenyl, $C_{1-6}$alkynyl, $C_{1-4}$alkoxy, $C_{3-8}$cycloalkyl$C_{1-4}$alkyl, or $(CH_2)_{0-3}R^j$;

$R^j$ is aryl, heteroaryl, $NR^eR^f$ or Het;

Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^e$ and $R^f$ are each independently selected from hydrogen, $C_{1-4}$alkyl and $C(O)C_{1-4}$alkyl;

or $R^e$, $R^f$ and the nitrogen atom to which they are attached form a heteroaliphatic ring of 4 to 7 ring atoms;

and $R^1$ and $R^2$ are optionally substituted by hydroxy, $C_{1-4}$alkyl, =O, $C(O)C_{1-4}$alkyl or $C_{3-8}$cycloalkyl;

or $R^1$, $R^2$ and the nitrogen atom to which they are attached form a heteroaliphatic ring of 4 to 7 ring atoms, which ring optionally contains 1, 2 or 3 additional heteroatoms selected from O and S or a group S(O), $S(O)_2$, NH or $NR^g$, where $R^g$ is $C_{1-4}$alkyl or heteroaryl, or said heteroaliphatic ring is fused to or substituted by a five- or six-membered nitrogen-containing heteroaliphatic ring, which heteroaliphatic ring is optionally spiro-fused and is optionally substituted by hydroxy, $C_{1-4}$alkyl, $C_{1-4}$alkoxy, $(CH_2)_{0-3}NR^hR^i$, aryl, heteroaryl, or a —$CH_2$— or —$CH_2CH_2$-alkylene bridge, where aryl and heteroaryl are optionally substituted by hydroxy, $C_{1-4}$alkyl or $C_{1-4}$alkoxy;

$R^h$ and $R^i$ are each independently selected from hydrogen, $C_{1-4}$alkyl and $C(O)C_{1-4}$alkyl, or $R^h$, $R^i$ and the nitrogen atom to which they are attached form, a heteroaliphatic ring of 4 to 7 ring atoms optionally substituted by $C_{1-4}$alkyl;

$R^3$ is hydrogen, $C_{1-6}$alkyl or $C_{2-6}$alkenyl;

$R^4$ is hydrogen or $C_{1-6}$alkyl;

X is

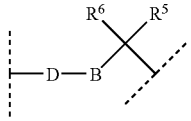

wherein $R^5$ and $R^6$ are each independently selected from hydrogen, halogen, $C_{1-4}$alkyl, $C_{2-4}$alkenyl or $C_{1-4}$alkoxy;

or $R^5$ and $R^6$ are linked to form a $C_{3-8}$cycloalkyl group;

B is aryl, heteroaryl, $CONR^7R^8$, optionally substituted by halogen, $C_{1-4}$alkyl, $C_{2-4}$alkenyl or $C_{1-4}$alkoxy;

$R^7$ is hydrogen or $C_{1-6}$alkyl;

or $R^7$ is linked to $R^5$ and/or $R^6$ to form a 5- to 10-membered ring, where said ring may be saturated, partially saturated or unsaturated, and where said ring is optionally substituted by halogen, $C_{1-4}$alkyl, $C_{2-4}$alkenyl, $C_{1-4}$alkynyl or $C_{1-4}$alkoxy;

$R^8$ is aryl or heteroaryl;

or $R^7$, $R^8$ and the nitrogen atom to which they are attached form a 5- to 10-membered mono- or bi-cyclic ring system, where said ring may be saturated, partially saturated or unsaturated, and where said ring is optionally substituted by halogen, $C_{1-4}$alkyl, $C_{2-4}$alkenyl, $C_{2-4}$alkynyl or $C_{1-4}$alkoxy;

D is a bond, $C_{1-6}$alkylene, $C_{2-6}$alkenylene, $C_{2-6}$alkynylene, aryl or heteroaryl, where said aryl or heteroaryl is optionally substituted by halogen, $C_{1-4}$alkyl or $C_{2-4}$alkenyl;

and pharmaceutically acceptable salts thereof.

A preferred class of compounds of formula (I) is that wherein E is a moiety containing at least one aromatic ring and possesses 5-, 6-, 9- or 10-ring atoms optionally containing 1, 2 or 3 heteroatoms independently selected from N, O and S, which ring is optionally substituted at any substitutable position by groups $Q^1$ and $Q^2$ as hereinbefore defined;

A more preferred class of compounds of formula (J) is that wherein E is a five- or six-membered aromatic ring optionally containing 1, 2 or 3 heteroatoms selected from N, O and S, which ring is optionally substituted at any substitutable position by groups $Q^1$ and $Q^2$ as hereinbefore defined.

Preferably, E is a six-membered aromatic ring optionally containing 1, 2 or 3 heteroatoms selected from N, O and S, which ring is optionally substituted by groups $Q^1$ and $Q^2$ as hereinbefore defined. More preferably, E is a six-membered ring optionally containing 1 or 2N atoms, such as phenyl, 1-pyridyl, 2-pyridyl, 3-pyridyl, pyridazinyl, pyrimidinyl and pyrazinyl, which ring is optionally substituted by groups $Q^1$ and $Q^2$ as hereinbefore defined. Most preferably, E is phenyl, 2-pyridyl or 3-pyridyl, optionally substituted by groups $Q^1$ and $Q^2$ as hereinbefore defined. Particularly, E is phenyl, optionally substituted by groups $Q^1$ and $Q^2$ as hereinbefore defined.

Also preferably, E is a five-membered aromatic ring optionally containing 1, 2 or 3 heteroatoms selected from N, O and S, which ring is optionally substituted by groups $Q^1$ and $Q^2$ as hereinbefore defined. More preferably, E is a five-membered ring containing 1 or 2 heteroatoms selected from N, O and S, such as 2-furanyl, 3-furanyl, 2-thienyl, 3-thienyl, pyrazolyl and imidazolyl, which ring is optionally substituted by groups $Q^1$ and $Q^2$ as hereinbefore defined. Most preferably, E is 3-furanyl, 2-thienyl or pyrazolyl, optionally substituted by groups $Q^1$ and $Q^2$ as hereinbefore defined. Particularly, E is 3-furanyl, optionally substituted by groups $Q^1$ and $Q^2$ as hereinbefore defined.

Another preferred class of compounds of formula (I) is that wherein E is $C_{3-8}$cycloalkyl. Preferably, E is $C_{3-6}$cycloalkyl. More preferably, E is cyclopropyl, cyclobutyl or cyclopentyl. Most preferably, E is cyclopropyl.

Preferably, $Q^1$ is halogen, hydroxy, $C_{1-4}$alkyl or $C_{1-4}$alkoxy. More preferably, $Q^1$ is fluorine, chlorine, methyl or methoxy. Most preferably, $Q^1$ is chlorine or methoxy.

A preferred class of compounds of formula (I) is that wherein A is $C_{1-6}$alkyl, $C_{2-6}$alkenyl or $C_{3-8}$cycloalkyl, where A is optionally substituted by halogen, hydroxy, $C_{1-4}$alkyl or $C_{1-4}$alkoxy. Preferably, A is $C_{3-8}$cycloalkyl preferably cyclopentyl or cyclohexyl, more preferably cyclohexyl, optionally substituted by halogen, hydroxy, $C_{1-4}$alkyl or $C_{1-4}$alkoxy.

Preferably, A is unsubstituted or substituted by fluorine, chlorine, methyl or methoxy. More preferably, A is unsubstituted.

A preferred class of compounds of formula (I) is that wherein $R^1$ is hydrogen, $C_{1-6}$alkyl, or $(CH_2)_{0-3}R^j$ wherein $R^j$ is as hereinbefore defined.

When $R^1$ is $(CH_2)_{0-3}R^j$ preferably $R^1$ is $CH_2Het$ wherein Het is as hereinbefore defined. Preferably, Het is a five- or six-membered heteroaliphatic ring containing a group $NC_{1-4}$alkyl, preferably NMe.

Preferably, $R^1$ is $C_{1-6}$alkyl, more preferably $C_{1-4}$alkyl, most preferably methyl.

A preferred class of compounds of formula (I) is that wherein $R^2$ is hydrogen, $C_{1-6}$alkyl or $C_{2-6}$alkenyl. Preferably, $R^2$ is hydrogen or methyl. More preferably, is methyl.

A further preferred class of compounds of formula (I) is that wherein $R^1$, $R^2$ and the nitrogen atom to which they are attached form a five- or six-membered heteroaliphatic ring, which ring optionally contains one additional oxygen atom or a group $NR^9$ wherein $R^8$ is as hereinbefore defined, which ring is optionally substituted by $(CH_2)_{0-3}NR^hR^i$ wherein $R^h$ and $R^i$ are as hereinbefore defined, preferably $NR^hR^i$ or $CH_2NR^hR^i$.

Preferably, $R^h$ is $C_{1-4}$alkyl, more preferably methyl.

Preferably, $R^1$ is $C_{1-4}$alkyl, more preferably methyl.

Preferably, the heteroaliphatic ring is morpholinyl.

A preferred class of compounds of formula (I) is that wherein $R^3$ is hydrogen, or $C_{1-4}$alkyl. Preferably, $R^3$ is hydrogen or methyl. More preferably, $R^3$ is hydrogen.

A preferred class of compounds of formula (I) is that wherein $R^4$ is hydrogen or $C_{1-4}$alkyl. Preferably, $R^4$ is hydrogen or methyl. More preferably, $R^4$ is hydrogen.

A preferred class of compounds of formula (I) is that wherein $R^5$ is hydrogen or $C_{1-4}$alkyl. Preferably, $R^5$ is hydrogen.

A further preferred class of compounds of formula (I) is that wherein $R^6$ is hydrogen or $C_{1-4}$alkyl. Preferably, $R^6$ is hydrogen.

A further preferred class of compounds of formula (I) is that wherein $R^a$ and $R^6$ are linked to form a cyclobutyl, cyclopentyl or cyclohexyl group. Preferably, $R^5$ and $R^6$ are linked to form a cyclopentyl group.

A preferred class of compounds of formula (I) is that wherein B is heteroaryl, $CONR^7$aryl or $CONR^7$heteroaryl, optionally substituted by halogen, $C_{1-4}$alkyl, $C_{2-4}$alkenyl or $C_{1-4}$alkoxy. Preferably, heteroaryl is pyrrolyl, furanyl, thienyl, pyridyl, pyrazolyl, indolyl, benzothienyl or benzimidazolyl.

Preferably, B is unsubstituted or substituted by $C_{1-4}$alkyl, particularly methyl. More preferably, B is unsubstituted.

When $R^7$ is present, preferably $R^7$ is hydrogen or $C_{1-4}$alkyl. More preferably, $R^7$ is hydrogen or methyl. Most preferably, $R^7$ is hydrogen.

When $R^7$ is present, also preferably $R^7$ is linked to $R^5$ to form a 5-, 6- or 8-membered ring, where said ring is optionally substituted by halogen, $C_{1-4}$alkyl, $C_{2-4}$alkenyl, $C_{2-4}$alkynyl or $C_{1-4}$alkoxy. Preferably, $R^7$ is linked to $R^5$ to form a six-membered ring.

A preferred class of compounds of formula (I) is that wherein D is a bond, $C_{1-4}$alkylene, $C_{2-4}$alkenylene or heteroaryl. Preferably, D is a bond, $C_{2-4}$alkenylene or furanyl. More preferably, D is $C_2$-alkenylene.

One favoured group of compounds of the present invention is of formula (Ia) and pharmaceutically acceptable salts thereof:

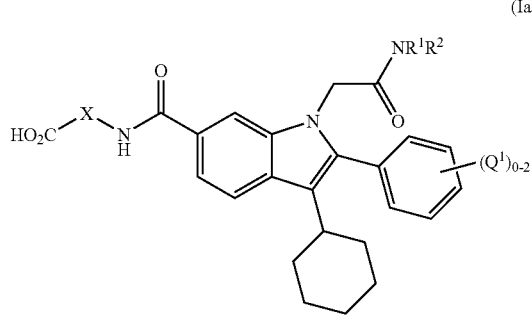

wherein $Q^1$, $R^1$, $R^2$ and X are defined in relation to formula (I).

Preferably, $Q^1$ is absent.

Preferably, $R^1$ is $C_{1-6}$alkyl, more preferably $C_{1-4}$alkyl, most preferably methyl.

Preferably, $R^2$ is $C_{1-6}$alkyl, more preferably methyl.

Preferably, $R^5$ is hydrogen.

Preferably, $R^6$ is hydrogen.

Preferably, $R^5$ and $R^6$ are linked to form a cyclobutyl, cyclopentyl or cyclohexyl group, more preferably a cyclopentyl group.

Preferably, B is $CONR^7R^8$, more preferably $CONR^7$aryl or $CONR^7$heteroaryl, most preferably $CONR^7$aryl, particularly $CONR^7$phenyl, where $R^7$ and $R^8$ are as defined in relation to formula (I). Preferably, $R^7$ is hydrogen.

Preferably, D is a bond or $C_2$-alkenylene.

Preferably, X is:

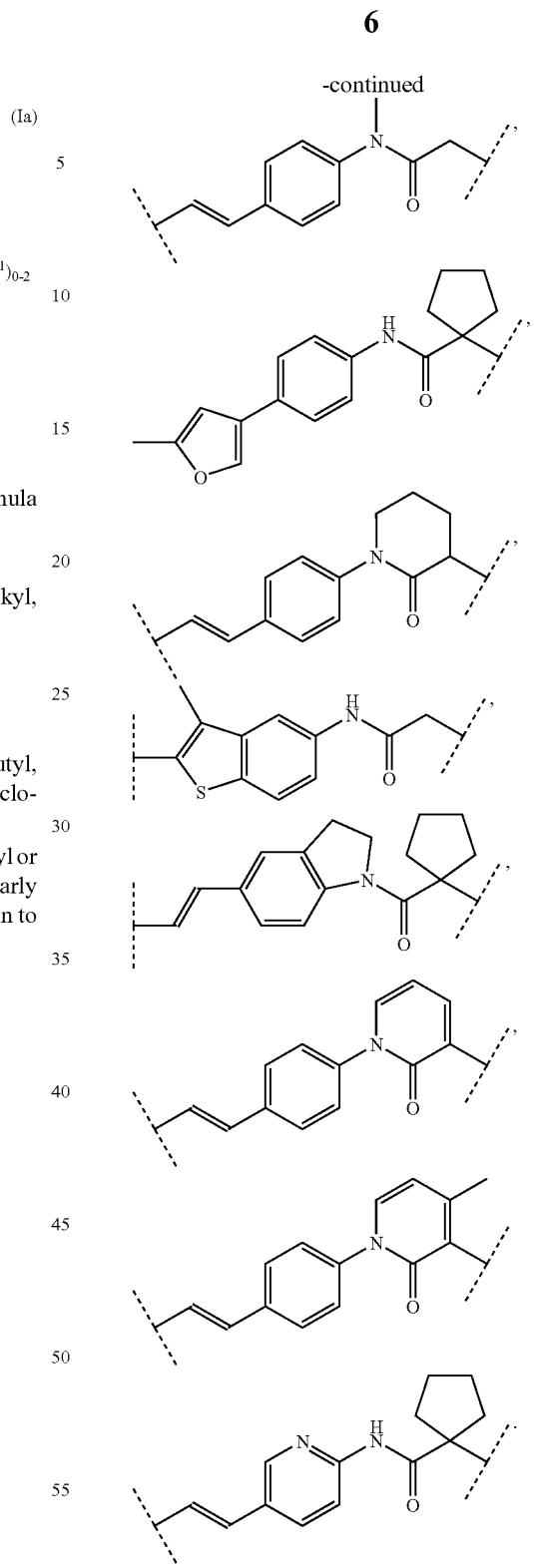

When any variable occurs more than one time in formula (I) or in any substituent, its definition on each occurrence is independent of its definition at every other occurrence.

As used herein, the term, "alkyl" or "alkoxy" as a group or part of a group means mat the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred, to herein may represent, for example, cyclopropyl, cyclobutyl, cyclopentyl or cyclohexyl A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. Suitable alkynyl groups are ethynyl and propargyl.

When used herein, the term "halogen" means fluorine, chlorine, bromine and iodine. Preferred halogens are fluorine and chlorine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl and quinolinyl.

Where a compound or group is described as "optionally substituted" one or more substituents may be present. Optional substituents are not particularly limited and may, for instance, be selected from $C_{1-6}$ alkyl, $C_{2-6}$ alkenyl, $C_{3-7}$ cycloalkyl, $C_{3-7}$ heterocycloalkyl, aryl, aryl($C_{1-6}$)alkyl, heteroaryl, heteroaryl($C_{1-6}$)alkyl, $C_{1-6}$ alkoxy, aryloxy, aryl($C_{1-6}$)alkoxy, heteroaryloxy, heteroaryl($C_{1-6}$)alkoxy, amino, nitro, halo, hydroxy, carboxy, formyl, cyano and trihalomethyl groups. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include:

(2E)-3-{4-[({1-[({3-cyclohexyl-1-[2-(dimethylamino)-2-oxoethyl]-2-phenyl-1H-indol-6-yl}carbonyl)amino]cyclopentyl}carbonyl)amino]-phenyl}-acrylic acid, (2E)-3-[4-({1-({[3-cyclohexyl-1-[2-(morpholin-4-yl-2-oxoethyl)-2-phenyl-1H-indol-6-yl]carbonyl}amino)cyclopentyl]carbonyl}amino)-phenyl]acrylic acid, (2E)-3-[4-({[1-({[3-cyclohexyl-1-[2-(dimethylamino)-2-oxoethyl]-2-(4-methoxyphenyl)-1H-indol-6-yl]carbonyl}amino)cyclopentyl]carbonyl}amino)phenyl]acrylic acid, (2E)-3-(2-{1-[({3-cyclohexyl-1-[2-(dimethylamino)-2-oxoethyl]-2-phenyl-1H-indol-6-yl}carbonyl)amino]cyclopentyl}-1H-benzimidazol-5-yl)acrylic acid, (2E)-3-[4-({[1-({[3-cyclohexyl-1-[2-(dimethylamino)-2-oxoethyl]-2-(6-methoxypyridin-3-yl)-1H-indol-6-yl]carbonyl}amino)cyclopentyl]carbonyl}amino)phenyl]acrylic acid, (2E)-3-[4-({[1-({[3-cyclohexyl-1-[2-(dimethylamino)-2-oxoethyl]-2-(1,3-oxazol-5-yl)-1H-indol-6-yl]carbonyl}amino)cyclopentyl]carbonyl}amino)phenyl]acrylic acid, (2E)-3-{4-[({1-[({3-Cyclohexyl-1-[2-(dimethylamino)-2-oxoethyl]-2-cyclopropyl-1H-indol-6-yl}carbonyl)amino]cyclopentyl}carbonyl)amino]phenyl}acrylic acid; and pharmaceutically acceptable salts thereof.

Further compounds within the scope of this invention include:

methyl (2E)-3-{4-[({1-[({3-cyclohexyl-1-[2-(dimethylamino)-2-oxoethyl]-2-phenyl-1H-indol-6-yl}carbonyl)amino]cyclopentyl}carbonyl)amino]phenyl}acrylate, (2E)-3-[4-({[1-({[3-cyclohexyl-1-(2-{methyl[(1-methylpiperidin-3-yl)methyl]amino}-2-oxoethyl)-2-phenyl-1H-indol-6-yl]carbonyl}amino)cyclopentyl]carbonyl}amino)-phenyl]acrylic acid, (2E)-3-{4-[({1-[({2-(4-chlorophenyl)-3-cyclohexyl-1-[2-(dimethylamino)-2-oxoethyl]-1H-indol-6-yl}carbonyl)amino]cyclopentyl}carbonyl)amino]phenyl}acrylic acid, (2E)-3-(4-{[N-({3-cyclohexyl-1-[2-(dimethylamino)-2-oxoethyl]-2-phenyl-1H-indol-6-yl}carbonyl)-N-methylglycyl]amino}phenyl)acrylic acid, 5-[({1-[({3-cyclohexyl-1-[2-(dimethylamino)-2-oxoethyl]-2-phenyl-1H-indol-6-yl}carbonyl)amino]cyclopentyl}carbonyl)amino]-3-methyl-1-benzothiophene-2-carboxylic acid, (2E)-3-{4-[[N-({3-cyclohexyl-1-[2-(dimethylamino)-2-oxoethyl]-2-phenyl-1H-indol-6-yl}carbonyl)glycyl](methyl)amino]phenyl}acrylic acid, 4-{4-[({1-[({3-cyclohexyl-1-[2-(dimethylamino)-2-oxoethyl]-2-phenyl-1H-indol-6-yl}carbonyl)amino]cyclopentyl}carbonyl)amino]phenyl}-2-furoic acid, (2E)-3-[4-({[1-({[3-cyclohexyl-1-[2-(dimethylamino)-2-oxoethyl]-2-(3-furyl)-1H-indol-6-yl]carbonyl}amino)cyclopentyl]carbonyl}amino)phenyl]acrylic acid, (2E)-3-(4-{3-[({3-cyclohexyl-1-[2-(dimethylamino)-2-oxoethyl]-2-phenyl-1H-indol-6-yl}carbonyl)amino]-2-oxopiperidin-1-yl}phenyl)acrylic acid, (2E)-3-{4-[({1-[({3-cyclohexyl-1-[2-(4-methylpiperazin-1-yl)-2-oxoethyl]-2-phenyl-1H-indol-6-yl}carbonyl)amino]cyclopentyl}carbonyl)amino]phenyl}acrylic acid, (2E)-3-{4-[({1-[({3-cyclohexyl-1-[2-(glycyl-amino)-2-oxoethyl]-2-phenyl-m-indol-6-yl}carbonyl)amino]cyclopentyl}carbonyl)amino]phenyl}acrylic acid, (2E)-3-[4-({[1-({[3-cyclohexyl-1-(2-oxo-2-{[(5-oxopyrrolidin-2-yl)methyl]amino}ethyl)-2-phenyl-1H-indol-6-yl]carbonyl}amino)cyclopentyl]-carbonyl}amino)phenyl]acrylic acid, (2E)-3-(4-{[(1-{[(3-cyclohexyl-1-{2-[4-(dimethylamino)piperidin-1-yl]-2-oxoethyl}-2-phenyl-1H-indol-6-yl)carbonyl]amino}cyclopentyl)carbonyl]-amino}phenyl)acrylic acid, (2E)-3-{4-[({1-[({3-cyclohexyl-1-[2-(methylamino)-2-oxoethyl]-2-phenyl-1H-indol-6-yl}carbonyl)amino]cyclopentyl}carbonyl)amino]phenyl}acrylic acid, (2E)-3-[1-({1-[({3-cyclohexyl-1-[2-(dimethylamino)-2-oxoethyl]-2-phenyl-1H-indol-6-yl}carbonyl)amino]cyclopentyl}carbonyl)-2,3-dihydro-1H-indol-5-yl]acrylic acid, (2E)-3-(4{[(1-{[(3-cyclohexyl-1-{2-[(1,4-dioxan-2-ylmethyl)amino]-1-oxoethyl}-2-phenyl-1H-indol-6-yl)carbonyl]amino}cyclopentyl)carbonyl]amino}phenyl)acrylic acid, (2E)-3-{4-[({1-[({3-cyclohexyl-1-[2-(1,1-dioxidothiomorpholin-4-yl)-2-oxoethyl]-2-phenyl-1H-indol-6-yl}carbonyl)amino]cyclopentyl}carbonyl)amino]phenyl}acrylic acid, (2E)-3-[4-({[1-({[3-cyclohexyl-1-(2-{2-[(dimethylamino)methyl]morpholin-4-yl}-2-oxoethyl)-2-phenyl-1H-indol-6-yl]carbonyl}amino)cyclopentyl]carbonyl}-amino)phenyl]acrylic acid, (2E)-3-{4-[({1-[({3-cyclopentyl-1-[2-(dimethylamino)-2-oxoethyl]-2-phenyl-1H-indol-6-yl}carbonyl)amino]cyclopentyl}carbonyl)amino]phenyl}acrylic acid,
(2E)-3-{4-[({1-[({3-cyclohexyl-1-[2-oxo-2-(3-pyrrolidin-1-ylpiperidin-1-yl)ethyl]-2-phenyl-1H-indol-6-yl}carbonyl)amino]cyclopentyl}carbonyl)amino]phenyl}acrylic acid,
(2E)-3-{4-[({1-[({3-cyclohexyl-1-[2-(dimethylamino)-2-oxoethyl]-1H-indol-6-yl}carbonyl)amino]cyclopentyl}carbonyl)amino]phenyl}acrylic acid,
(2E)-3-{4-[3-[({3-cyclohexyl-1-[2-(dimethylamino)-2-oxoethyl]-2-phenyl-1H-indol-6-yl}carbonyl)amino]-2-oxopyridin-1(2H)-yl]phenyl}acrylic acid,
(2E)-3-{4-[3-[({3-cyclohexyl-1-[2-(dimethylamino)-2-oxoethyl]-2-phenyl-1H-indol-6-yl}carbonyl)amino]-4-methyl-2-oxopyridin-1(2H)-yl]phenyl}acrylic acid,
(2E)-3-[4-({[1-({[1-(2-{[2-(acetylamino)ethyl]amino}-2-oxoethyl)-3-cyclohexyl-2-phenyl-1H-indol-6-yl]carbonyl}amino)cyclopentyl]carbonyl}amino)phenyl]acrylic acid,
(2E)-3-{4-[({1-[({3-cyclohexyl-1-[2-(dimethylamino)-2-oxoethyl]-2-methyl-1H-indol-6-yl}carbonyl)amino]cyclopentyl}carbonyl)amino]phenyl}acrylic acid,
(2E)-3-{4-[({1-[({3-cyclohexyl-2-{3-[(dimethylamino)methyl]phenyl}-1-[2-(dimethylamino)-2-oxoethyl]-1H-indol-6-yl}carbonyl)amino]cyclopentyl}carbonyl)amino]phenyl}acrylic acid,
(2E)-3-{6-[({1-[({3-cyclohexyl-1-[2-(dimethylamino)-2-oxoethyl]-2-phenyl-1H-indol-6-yl}carbonyl)amino]cyclopentyl}carbonyl)amino]pyridin-3-yl}acrylic acid,
(2E)-3-[4-({[1-({[3-cyclohexyl-2-cyclopropyl-1-(2-morpholin-4-yl-2-oxoethyl)-1H-indol-6-yl]carbonyl}amino)cyclopentyl]carbonyl}amino)phenyl]acrylic acid,
(2E)-3-{4-[({1-[({3-cyclohexyl-2-cyclopropyl-1-[2-(4-methylpiperazin-1-yl)-2-oxoethyl]-1H-indol-6-yl}carbonyl)amino]cyclopentyl}carbonyl)amino]phenyl}acrylic acid;

and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically-acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drag molecule. The transformation in viva may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for tire treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation, of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (A), compounds of formula (I) may be prepared by reacting a compound of formula (II) with a compound of formula (III):

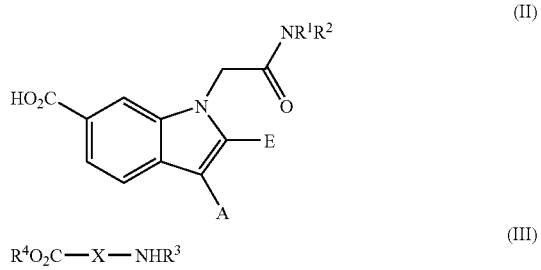

(II)

$R^4O_2C$—X—$NHR^3$ (III)

wherein $R^1$, $R^2$, A, E, X, $R^3$ and $R^4$ are as defined for formula (I). The reaction is conveniently performed in the presence of a coupling reagent, such as O-(7-azabenzotriazol-1-yl)-N,N,N',N'-tetramethyluronium hexafluorophosphate, and a base, such as diisopropylethylamine, in a solvent.

Suitable solvents include dimethylformamide and dichloromethane.

Further details of suitable procedures will be found in the accompanying Examples. For instance, compounds of formula (I) can be converted into other compounds of formula (I) using synthetic methodology well known in the art.

Compounds of formulae (II) and (III) are either well known in the art or may be prepared by conventional methodology well known to one of ordinary skill in die art using, for instance, procedures described in the accompanying Examples, or by alternative procedures which will be readily apparent.

For example, compounds of formula (II) may be prepared by reacting a compound of formula (IV) with a compound of formula (V):

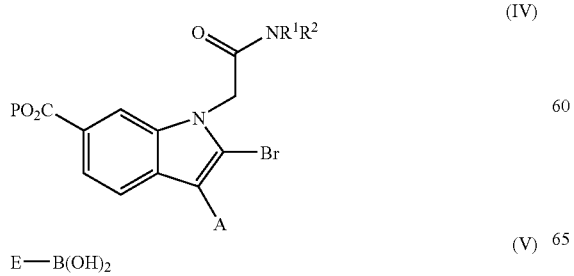

(IV)

E—B(OH)$_2$ (V)

wherein $R^1$, $R^2$, A and E are as defined for formula (I) and P is a suitable protecting group.

The reaction is effected in the presence of a Pd(0) catalyst under conditions typical for the Suzuki reaction.

Other substituted indoles can be made via the Fischer indole methodology well known to the person skilled in the art.

Compounds of formula (IV) may be prepared by reacting a compound of formula (VI) with a compound of formula (VII):

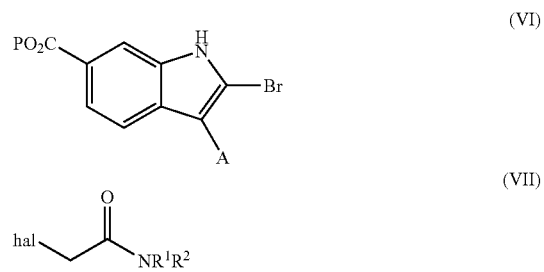

(VI)

(VII)

wherein A, $R^5$ and $R^2$ are as defined for formula (I), P is a suitable protecting group and hal is a halogen atom, preferably chlorine or bromine. The reaction is effected by treatment of the compound of formula (VI) with a deprotonating agent, such as sodium hydride, followed by addition of the compound of formula (VII).

The compound of formula (VI) where A is cyclohexyl may be prepared from the compound of formula (VIII);

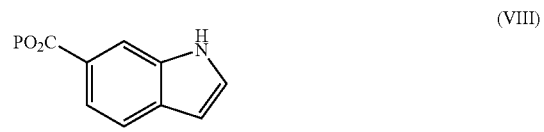

(VIII)

wherein P is a suitable protecting group, by alkylation at the 3-position of the compound of formula (VIII) using a deprotonating agent, such as sodium methoxide, and cyclohexanone, in a suitable solvent, such as methanol. The alkylated product is then, hydrogenated to remove the double bond of the cyclohexenyl group. Suitable hydrogenation conditions include the use of hydrogen in the presence of a catalyst, such as Pearlman's catalyst. The hydrogenated product is then brominated at the 2-position of the indole ring using a suitable brominating agent, such as NBS. The compound of formula (VI) may then be reacted with the compound of formula (VII) as hereinbefore described, or, alternatively, may be reacted with a compound of formula (V), under conditions described for the preparation of the compounds of formula (II), to prepare compounds of formula (IX):

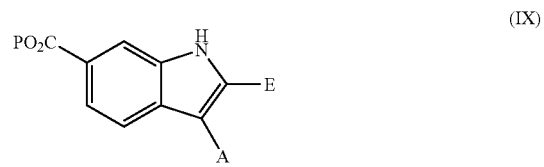

(IX)

The compound of formula (IX) may then be reacted with the compound of formula (VII), under conditions described for the preparation of the compounds of formula (IV), as an alternative way of preparing the compounds of formula (II).

As an alternative to the compound of formula (VII), the compound of formula (X) may be used:

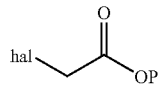

(X)

where P is a suitable protecting group and hal is a halogen atom, preferably chlorine or bromine. The protecting group is removed under suitable conditions, depending on die group. Suitable conditions for deesterification may include acid or base hydrolysis or hydrogenation. The carboxylic acid may then be converted to the amide using $HNR^1R^2$.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples are illustrative of this invention.

The compounds of the invention were tested for inhibitory activity against the HCV RNA dependent RNA polymerase (NS5B) in an enzyme inhibition assay (example i)) and in a cell based sub-genomic replication assay (example ii)). The compounds generally have IC50's below 1 μM in the enzyme assay and several examples have low 0.5 μM in the cell based assay.

i) In-Vitro HCV NS5B Enzyme Inhibition Assay

WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated OTP or NTPs is quantified by measuring acid-insoluble radioactivity. The present inventors have employed this assay to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM $MgCl_2$, 1 mM DTT, 50 mM NaCl, 0.03% N-octylglucoside, 1 μCi [$^3$H]-UTP (40 Ci/mmol, NEN), 10 μM UTP and 10 μg/ml poly(A) or 5 μM NTPs and 5 μg/ml heteropolymeric template. Oligo(U)$_{12}$ (1 μg/ml, Genset) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1M $Na_2HPO_4/NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

% Residual activity=$100/(1+[I]/IC_{50})^s$ where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to $I_{377}$neo/NS3-37 wt described by Lohmann et al (1999) (EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International patent application WO 02/59321). Cells were seeded into 96 well plates at a density of $10^4$ cells per well in a final volume of 0.1 ml of DMEM/10% FCS. Two hours after plating, 50 μl of DMEM/10% FCS containing a 3× concentration of inhibitor were added, cells were incubated for 96 hours and then fixed for 10' with ice-cold isopropanol. Each condition was tested in duplicate and average absorbance values were used for calculations. The cells were washed twice with PBS, blocked with 5% non-fat dry milk in PBS+ 0-1% Triton X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at $^{405}/_{620}$ nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, Fraction inhibition=$1-(Ai-b)/(A_0-b)=[I]^n/([I]^n+IC_{50})$ where:
Ai=absorbance value of HBI10 cells supplemented with the indicated inhibitor concentration.
$A_0$=absorbance value of HBI10 cells incubated without inhibitor.
b=absorbance value of Huh-7 cells plated at the same density in the same microtiter plates and incubated without inhibitor.
n=Hill coefficient.

iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al, J. Org. Chem. 1978, 43, 2923) or on semi-automated flash chromatography systems utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using die residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a Perkin Elmer API 100 operating in negative (ES⁻) or positive (ES⁺) ionization mode and results are reported as the ratio of mass over charge (m/z) for the parent ion only. Preparative scale HPLC separations were carried out on a Waters Delta Prep 4000 separation module, equipped with a Waters 486 absorption detector or on a Gilson preparative system. In all cases compounds were eluted with linear gradients of water and acetonitrile both containing 0.1% TEA using flow rates between 15 and 25 mL/min.

The following abbreviations are used in the examples, the schemes and the tables:

DCM: dichloromethane; DBEA: diisopropylethylamine; DME: dimethoxyethane; DMF: dimethylformamide; DMSO: dimethylsulfoxide; eq.: equivalent(s); EtOAc: ethyl acetate; Et$_2$O: diethyl ether; EtOH: ethanol; h: hour(s); HATU: O-(7-azabenzotriazol-1-yl)-N,N,N',N'-tetramethyluronium hexafluorophosphate; Me: methyl; MeCN: acetonitrile; MeOH: methanol; min: minutes; NBS: N-bromo succinimide; PE: petroleum ether; Ph: phenyl; RP-HPLC: reversed phase high-pressure liquid chromatography; RT: room temperature; TFA: trifluoroacetic acid; THF: tetrahydrofuran; TMS: trimethylsilyl.

EXAMPLE 1

Preparation of (2E)<3-{4-[({1-[({3-Cyclohexyl-1-[2-(dimethylamino)-2-oxoethyl]-2-phenyl-1H-indol-6-yl}carbonyl)amino]cyclopentyl}carbonyl)amino]phenyl}acrylic acid Step 1:
3-Cyclohex-1-en-1-yl-1H-indole-6-carboxylic acid To a solution of methyl-indole-6-carboxylate in MeOH (1.7 M) was added cyclohexanone (3.0 eq.) followed by 30% NaOMe in MeOH (6.0 eq.) in 100 ml portions over 20 min. The resulting mixture was stirred at RT for 45 min and refluxed for 8 h. Water was added, and the mixture stirred at RT until all solids had dissolved. The organic solvent was removed under vacuum and the pH of the aqueous phase adjusted to 1, by slow addition of concentrated HCl at 0° C. The precipitate was isolated by filtration, and then washed with water, until the pH of the water reached 6-7. Drying under high, vacuum gave the title compound as a beige solid (100%). $^1$H NMR (300 MHz, DMSO-d$_6$, 300 K) δ 1.49-1.98 (m, 8H), 6.22 (bs, 1H), 7.50 (s, 1H), 7.64 (d, J 7.6, 1H), 7.75 (d, J 7.6, 1H), 8.02 (s, 1H), 11.39 (s, 1H); MS (ES⁺) m/z 242 (M+H)⁺.

Step 2: methyl 3-cyclohexyl-1H-indole-6-carboxylate

A solution (0.5 M) of 3-cyclohexenyl-1H-indole-6-carboxylic acid (from Step 1) in THF/MeOH (0.5 M, 1:1, v/v) was hydrogenated for 14 h over Pd(OH)$_2$/C (0.1 eq., 20%) at 60 psi. The catalyst was removed by filtration on a pad of Celite™ and the filtrate evaporated to dryness to afford 3-cyclohexyl-1H-indole-6-carboxylic acid (90%) as a white solid. $^1$H NMR (300 MHz, DMSO-d$_6$, 300 K) δ 1.20-1.53 (m, 5H), 1.70-1.87 (m, 3H), 1.90-2.02 (m, 2H), 2.69-2.86 (m, 1H), 7.40 (s, 1H), 7.55-7.65 (m, 2H), 8.0 (s, 1H), 11.40 (s, 1H); MS (ES⁺) m/z 244 (M+H)⁺.

A solution of the foregoing compound in MeOH (0.4 M) was treated at 0° C. with thionylchloride (0.5 eq.) and refluxed for 24 h. Volatiles were removed under vacuum to afford the title compound (100%) as a solid. $^1$H NMR (300 MHz, DMSO-d$_6$, 300 K) δ 1.22-1.53 (m, 5H), 1.70-1.86 (m, 3H) δ 1.90-2.02 (m, 2H), 2.69-2.86 (m, 1H), 3.89 (s, 3H), 7.42 (s, 1H), 7.55-7.70 (m, 2H), 8.05 (s, 1H); MS (ES⁺) m/z 258 (M+H)⁺.

Step 3: methyl 2-bromo-3-cyclohexyl-1H-indole-6-carboxylate

To a solution (0.14 M) of methyl 3-cyclohexyl-1H-indole-6-carboxylate (from Step 2) in CCl$_4$ was added freshly crystallized NBS (1.1 eq.) portionwise over a period of 1 h at RT. The resulting mixture was stirred for 2 h at RT, then washed with water (3×) and a saturated aqueous solution of sodium thiosulfate (2×). After phase cut, the aqueous phases were back-washed with EtOAc and die combined organic phases dried over Na$_2$SO$_4$ and evaporated. The resulting brown solid was dissolved in hot DCM and filtered rapidly over a pad of silica-gel using DCM as the eluant to give the title compound (49.6%) as a solid, $^1$H NMR (300 MHz, DMSO-d$_6$, 300 K) δ 1.32-1.48 (m, 3H), 1.65-1.99 (m, 7H), 2.69-2.89 (m, 1H), 3.89 (s, 3H), 7.59 (d, J 7.6, 1H), 7.75 (d, J 7.6, 1H), 7.92 (s, 1H), 12.02 (br s, 1H); MS (ES⁺) m/z 337 (M+H)⁺.

Step 4: Methyl 3-cyclohexyl-2-phenyl-1H-indole-6-carboxylate

To a solution of methyl 2-bromo-3-cyclohexyl-1H-indole-6-carboxylate (from Step 3) in DME and EtOH (0.2 M, 3:1, v/v) was added phenyl-boronic acid (1.2 eq.) followed by 2 M aqueous Na$_2$CO$_3$ (8.5 eq,). The mixture was degassed with ultrasound for 30 min, then Pd(PPh$_3$)$_4$ (0.1 eq.) was added and mixture degassed with ultrasound for a further 30 min. The reaction was stirred under nitrogen at 90° C. for 6 h and then cooled to RT. Water was added and the solids filtered off. They were washed with Et$_2$O to give the title compound (49%). The combined mother liquors together with the reaction solvents were washed with water (150 ml) and after phase-cut the organic phase was dried over Na$_2$SO$_4$ and evaporated to dryness. The residual solid was crystallized from boiling CHCl$_3$ to give more title compound (38%, 87% total yield). $^1$H NMR (400 MHz, DMSO-d$_6$, 300 K) δ 1.21-1.48 (m, 3H), 1.65-1.80 (m, 5H), 1.90-2.05 (m, 2H), 2.79-2.95 (m, 1H), 3.88 (s, 3H), 7.2-7.34 (m, 1H), 7.40-7.50 (m, 1H), 7.51-7.60 (m, 3H), 7.60 (d, J 7.6, 1H), 7.84 (d, J 7.6, 1H), 8.00 (s, 1H); MS (ES⁺) m/z 334 (M+H)⁺.

Step 5: tert-Butyl 3-cyclohexyl-2-phenyl-1H-indole-6-carboxylate

Methyl 3-cyclohexyl-2-phenyl-1H-indole-6-carboxylate (from Step 4) was dissolved in THF (0.2 M) and treated with aqueous KOH (2 eq., 1 M solution). The resulting mixture was heated to 80° C. for 4 h and then cooled to RT. The mixture was diluted with water and extracted with EtOAc (2×). The aqueous phase was acidified to pH 2 using hydrochloric acid (1 M) and then extracted with DCM and EtOAc. Drying over Na$_2$SO$_4$ and evaporation left a grey powder, which was dissolved in DCM (0.3 M). tert-Butyl N,N'-diisopropylimidocarbamate (2 eq.) was added in one portion, and the mixture stirred overnight. Another 2 eq. of the imidocarbamate were added at this point, and the heterogeneous mixture was stirred for another 24 h. Evaporation gave a white powder, which was loaded onto a column containing silica gel. Elution with PE/EtOAc (10:1) gave the title compound as an off-white solid. $^1$H NMR (400 MHz, CDCl$_3$, 300K) δ 1.30-1.47 (m, 3H), 1.62 (s, 9H), 1.74-1.96 (m, 5H), 1.99-2.16 (m, 2H), 2.95 (t, J 12.4, 1H), 7.40-7.48 (m, 1H), 7.49-7.61 (m, 4H), 7.74 (d, J 8.6, 1H), 7.84 (d, J 8.6, 1H), 8.05 (s, 1H), 8.11 (bs, 1H). MS (ES$^+$) m/z 376 (M+H)$^+$.

Step 6: 3-Cyclohexyl-1-[2-(dimethylamino)-2-oxoethyl]-2-phenyl-1H-indole-6-carboxylic acid Tert-Butyl 3-cyclohexyl-2-phenyl-1H-indole-6-carboxylate (from Step 5) was dissolved in DMF (0.18 M). NaH (60% suspension in mineral oil, 1.5 eq.) was added and the resultant mixture stirred for 5 min at RT, then for another 5 min at 50° C. The solution was allowed to reach RT, and then neat 2-chloro-N,N-dimethylacetamide (1.6 eq.) was added dropwise. After 1 h analytical RP HPLC indicated complete conversion of the starting material. The mixture was diluted with EtOAc, and then washed with water (3×) and brine. Drying over Na$_2$SO$_4$ and evaporation gave a colorless solid, which was purified by flash chromatography on silica gel using PE/EtOAc (3:1, then 2:1) as the eluent. The resulting colorless solid was immediately dissolved in a mixture of DCM and TFA (0.05 M, 1:1, v/v). After stirring for 30 min at RT, the solvents were removed in vacuo to give after drying under high-vacuum, the title compound as a light yellow foam. $^1$H NMR (400 MHz, DMSO-d$_6$, 300 K) δ 1.12-1.31 (m, 3H), 1.60-1.75 (m, 5H), 1.80-1.92 (m, 2H), 2.53-2.59 (m, 1H), 2.80 (s, 3H), 2.89 (s, 3H), 4.84 (s, 2H), 7.31 (d, J 6.4, 2H), 7.48-7.53 (m, 3H), 7.64 (d, J 8.4, 1H), 7.81 (d, J 8.4, 1H), 7.92 (s, 1H,); MS (ES$^+$) m/z 405 (M+H)$^+$ Step 7: Ethyl (2E)-3 (4-{[(1-aminocyclopentyl)carbonyl]amino}phenyl)acrylate 1-{[(benzyloxy)carbonyl]amino}cyclopentanecarboxylic acid was dissolved in DMF (0.2 M). HATU (1 eq.) and triethylamine (3 eq.) were added, followed by ethyl cinnamate (0.95 eq.). The resulting mixture was stirred for 48 h at 40° C. DMF was evaporated, the resulting oil taken up in EtOAc and the solution washed with HCl (3×, 1 M), water, a solution of saturated aqueous NaHCO$_3$ (2×) and brine. Drying over Na$_2$SO$_4$ and evaporation gave an orange solid, which was purified by flash chromatography on silica gel using PE/EtOAc (2.5:1, containing 1% EtOH) as the eluent. The resulting solid was immediately dissolved in DCM (0.1M) and triflic acid (5 eq.) was added dropwise at RT. After 5 min at RT, the red mixture was poured into an aqueous solution of NaHCO$_3$. The organic phase was separated, the aqueous phase was extracted with DCM (4×) and the combined organic phases dried over Na$_2$SO$_4$. Evaporation gave the title compound as an off-white solid, which was used without further purification. $^1$H NMR (400 MHz, DMSO-d$_6$, 300 K) δ 1.26 (t, J 7.1, 3H), 1.48-1.61 (m, 2H), 1.63-1.87 (m, 4H), 1.96-2.10 (m, 2H), 4.18 (q, J 7.1, 2H), 6.53 (d, J 16.0, 1H), 6.60-7.30 (bs, 3H), 7.59 (d, J 16.0, 1H), 7.67 (d, J 8.5, 2H), 7.76 (d, J 8.5, 2H); MS (ES$^+$) m/z 303 (M+H)$^+$.

Step 8: (2E)-3-{4-[({1-[({3-Cyclohexyl-1-[2-(dimethylamino)-2-oxoethyl]-2-phenyl-1H-indol-6-yl}carbonyl)amino]cyclopentyl}carbonyl)amino]phenyl}-acrylic acid A solution of 3-cyclohexyl-1-[2-(dimethylamino)-2-oxoethyl]-2-phenyl-1H-indole-6-carboxylic acid (from Step 6) in DMF (0.1 M) was treated with DIPEA (2 eq.), HATU (1.1 eq.) and ethyl (2E)-3-(4-{[(1-aminocyclopentyl)carbonyl]amino}phenyl)acrylate (from Step 7, 1.1 eq.). The solution was stirred at 25° C. for 12 h, then for 24 h at 50° C. The mixture was diluted with EtOAc, and then washed sequentially with HCl (2×, 1 N), NaOH (2×, 1N) and brine. The organic layer was dried over Na$_2$SO$_4$ and concentrated to afford an oil, which was dissolved in a mixture of THF and MeOH (0.5M, 2:1, v/v). NaOH (2 eq., 1 N) was added and the resultant mixture stirred at 50° C. for 1 h. The reaction mixture was diluted with EtOAc, and then washed with HCl (2×, 1 N), brine, and dried over Na$_2$SO$_4$. Evaporation gave an off-white foam, which was purified by RP-HPLC (column: Waters X-terra C18, 19×150 mm, 5 micron; flow 20 mL/min) to give the title compound (45%) as a white powder after lyophilization. $^1$H NMR (400 MHz, DMSO-d$_6$, 300 K) δ 1.11-1.39 (m, 3H), 1.60-1.96 (m, 11H), 2.03-2.17 (m, 2H), 2.28-2.40 (m, 2H), 2.61 (m, 1H), 2.81 (s, 3H), 2.88 (s, 3H), 4.84 (s, 2H), 6.40 (d, J 16.0, 1H), 7.32 (d, J 6.4, 2H), 7.46-7.55 (m, 4H), 7.59 (d, J 8.4, 2H), 7.65 (d, J 8.4, 2H), 7.71 (d, J 8.2, 1H), 7.80 (d, J 8.2, 1H), 7.86 (s, 1H), 8.27 (s, 1H), 9.67 (s, 1H), 12.1 (bs, 1H). MS (ES$^+$) m/z 661 (M+H)$^+$.

As a second fraction, methyl (2E)-3-{4-[({1-[({3-cyclohexyl-1-[2-(dimethylamino)-2-oxoethyl]-2-phenyl-1H-indol-6-yl}carbonyl)amino]cyclopentyl}carbonyl)amino]phenyl}acrylate (4%) was obtained. $^1$H NMR (400 MHz, DMSO-d$_6$, 300 K) δ 1.10-1.40 (m, 3H), 1.60-1.97 (m, 11H), 2.03-2.16 (m, 2H), 2.28-2.40 (m, 2H), 2.57 (m, 1H), 2.77 (s, 3H), 2.88 (s, 3H), 3.71 (s, 3H), 4.83 (s, 2H), 6.51 (d, J 16.0, 1H), 7.32 (d, J 6.5, 2H), 7.47-7.53 (m, 3H), 7.54 (d, J 16.0, 1H), 7.58-7.69 (m, 4H), 7.71 (d, J 8.4, 1H), 7.80 (d, J 8.4, 1H), 7.86 (s, 1H), 8.27 (s, 1H), 9.69 (s, 1H). MS (ES$^+$) m/z 675 (M+H)$^+$.

EXAMPLE 2

Preparation of (2E)-3-[4-({[1-({[3-Cyclohexyl-1-[2-(morpholin-4-yl-2-oxoethyl)-2-phenyl-1H-indol-6-yl]carbonyl}amino)cyclopentyl]carbonyl}amino)-phenyl]acrylic acid Following the procedure described in Example 1, but utilizing 4-(chloroacetyl)morpholine instead of 2-chloro-N,N-dimethylacetamide in step 6, the title compound (42%) was obtained as a colorless powder after lyophilization. $^1$H NMR (400 MHz, DMSO-d$_6$, 330 K) δ 1.15-1.39 (m, 3H), 1.61-1.95 (m, 11H), 2.07-2.20 (m, 2H), 2.29-2.42 (m, 2H), 2.61 (m, 1H), 3.33-3.41 (m, 4H), 3.41-3.52 (m, 4H), 4.86 (s, 2H), 6.38 (d, J 16.0, 1H), 7.33 (d, J 7.4, 2H), 7.47-7.56 (m, 4H), 7.58 (d, J 8.7, 2H), 7.63 (d, J 78.7, 2H), 7.67 (d, J 8.4, 1H), 7.79 (d, J 8.4, 1H), 7.90 (s, 1H), 8.11 (s, 1H), 9.56 (s, 1H). MS (ES+) m/z 703 (M+H)$^+$.

EXAMPLE 3

Preparation of (2E)-3-[4-({[1-({[3-cyclohexyl-1-[2-(dimethylamino)-2-oxoethyl]-2-(4-methoxyphenyl)-1H-indol-6-yl]carbonyl}amino)cyclopentyl]carbonyl}amino)phenyl]acrylic acid Step 1: Methyl 2-bromo-1-(2-tert-butoxy-2-oxoethyl)-3-cyclohexyl-1H-indole-6-carboxylate A solution (0.1 M) of methyl 2-bromo-3-cyclohexyl-1H-indole-6-carboxylate in DMF was treated at 0° C. with NaH (1.3 eq.) and then stirred at 25° C. for 1 h. The solution was treated with tert-butylbromoacetate (1.2 eq.) and stirred 25°

C. for 12 h. The mixture was diluted with EtOAc and washed sequentially with HCl (1 N) and brine. The dried organic phase was concentrated and the residue purified by flash chromatography on silica gel (5:95 EtOAc/PE) to afford the title compound (83%) as a colorless solid. $^1$H NMR (300 MHz, DMSO-$d_6$, 300 K) δ 1.31-1.53 (m, 3H), 1.42 (s, 9H), 1.64-2.02 (m, 7H), 2.77-2.96 (m, 1H), 3.88 (s, 3H), 5.12 (s, 2H), 7.68 (dd, J 8.4, 1.2, 1H), 7.84 (d, J 8.4, 1H), 8.16 (d, J 1.2, 1H); MS (ES$^+$) m/z 452 (M+H)$^+$.

Step 2: Methyl 1-(2-tert-butoxy-2-oxoethyl)-3-cyclohexyl-2-(4-methoxyphenyl)-1H-indol-6-carboxylate A solution (0.1 M) of methyl 2-bromo-1-(2-tert-butoxy-2-oxoethyl)-3-cyclohexyl-1H-indole-6-carboxylate (from Step 1) in DME and EtOH (5:2) was treated with 4-methoxyphenylboronic acid (1.5 eq.). Aqueous Na$_2$CO$_3$ (2 N, 8.5 eq.) was added and the solution was degassed, and then heated with Pd(PPh$_3$)$_4$ (0.1 eq.). The mixture was heated at 80° C. for 2 h, then cooled and diluted with EtOAc and brine. The organic phase was separated, dried and concentrated under reduced pressure. The residue was purified by filtration through silica gel (5:95 EtOAc/PE) to give the title compound (81%) as a solid. $^1$H NMR (300 MHz, DMSO-$d_6$, 300K) δ 1.13-1.38 (m, 3H), 1.33 (s, 9H), 1.61-1.96 (m, 7H), 2.55-2.67 (m, 1H), 3.86 (s, 3H), 3.88 (s, 3H), 4.73 (s, 2H), 7.11 (d, J 8.6, 2H), 7.27 (d, J 8.6, 2H), 7.69 (dd, J 8.4, 1.1, 1H), 7.86 (d, J 8.4, 1H), 8.06 (d, J 1.1, 1H).

Step 3: [3-Cyclohexyl-6-(methoxycarbonyl)-2-(4-methoxyphenyl)-1H-indol-1-yl]acetic acid A solution (0.4 M) of methyl 1-(2-tert-butoxy-2-oxoethyl)-3-cyclohexyl-2-(4-methoxyphenyl)-1H-indole-6-carboxylate (from Step 2) in a 1:1 mixture of CH$_2$Cl$_2$/TFA was stirred at 25° C. for 4 h. The mixture was concentrated and the residue was triturated with Et$_2$O to afford the title compound (95%) as a solid. $^1$H NMR (300 MHz, DMSO-$d_6$, 300K) δ 1.13-1.36 (m, 3H), 1.62-1.95 (m, 7H), 2.56-2.67 (m, 1H), 3.86 (s, 3H), 3.89 (s, 3H), 4.74 (s, 2H), 7.12 (d, J 8.6, 2H), 7.28 (d, J 8.6, 2H), 7.69 (dd, J 8.5, 1.2, 1H), 7.86 (d, J 8.5, 1H), 8.02 (d, J 1.2, 1H), 12.98 (bs, 1H).

Step 4: 3-Cyclohexyl-1-[2-(dimethylamino)-2-oxoethyl]-2-(4-methoxyphenyl)-1H-indole-6-carboxylic acid A solution (0.04 M) of [3-cyclohexyl-6-(methoxycarbonyl)-2-(4-methoxyphenyl)-1H-indol-1-yl]acetic acid (from Step 3) in CH$_2$Cl$_2$ was treated with DIPEA (4 eq.), HATU (2 eq.) and dimethylamine hydrochloride (1.5 eq.). The solution was stirred at 25° C. for 12 h. The mixture was diluted with EtOAc and then washed sequentially with aqueous HCl (1 N), NaOH (2 N) and brine. The dried organic layer was concentrated and the residue dissolved in a 1:1 mixture of THF/H$_2$O. The resulting solution (0.05 M) was treated with aqueous KOH (1 N, 4 eq.), then stirred at 70° C. for 16 h. The mixture was concentrated under reduced pressure and the residue was treated with aqueous HCl (1 N) and extracted with EtOAc. The dried organic phase was washed with brine, dried and then concentrated to give the title compound (91%) as a solid. $^1$H NMR (300 MHz, DMSO-$d_6$, 300K) δ 1.14-1.35 (m, 3H), 1.63-1.98 (m, 7H), 2.54-2.65 (m, 1H), 2.83 (s, 3H), 2.94 (s, 3H), 3.85 (s, 3H), 4.86 (s, 2H), 7.09 (d, J 8.6, 2H), 7.25 (d, J 8.6, 2H), 7.66 (d, J 8.4, 1H), 7.82 (d, J 8.4, 1H), 7.92 (s, 1H), 12.45 (br s, 1H); MS (ES$^+$) m/z 435 (M+H)$^+$.

Step 5: (2E)-3-[4-({[1-({[3-cyclohexyl-1-[2-(dimethylamino)-2-oxoethyl]-2-(4-methoxyphenyl)-1H-indol-6-yl]carbonyl}amino)cyclopentyl]carbonyl}amino)-phenyl]acrylic acid A solution (0.04 M) of 3-cyclohexyl-1-[2-(dimethylamino)-2-oxoethyl]-2-(4 methoxyphenyl)-1H-indole-6-carboxylic acid (from Step 4) in DMF was treated with DIPEA (3 eq.), HATU (2 eq.) and ethyl (2E)-3-(4-{[(1-aminocyclopentyl)carbonyl]amino}phenyl)acrylate (1.1 eq.). The solution was stirred at 25° C. for 12 h. The mixture was diluted with EtOAc then washed sequentially with aqueous HCl (1N), NaOH (2 N) and brine. The dried organic layer was concentrated and the residue dissolved in a solution 1:1 of THF/H$_2$O. The resulting solution was treated with LiOH monohydrate (3 eq.) and stirred at 50° C. for 5 h. The mixture was concentrated under reduced pressure and the residue was treated with aqueous HCl (1 N). Purification by HPLC (stationary phase: Water Symmetry C18 19×300 mm) gave the title compound (11%) as a solid. $^1$H NMR (400 MHz, DMSO-$d_6$, 300K) δ 1.11-1.40 (m, 3H), 1.62-1.91 (m, 11H), 2.05-2.16 (m, 2H), 2.28-2.44 (m, 2H), 2.50-2.62 (m, 1H), 2.80 (s, 3H), 2.92 (s, 3H), 3.85 (s, 3H), 4.83 (s, 2H), 6.40 (d, J 16.0, 1H), 7.08 (d, J 8.6, 2H), 7.24 (d, J 8.6, 2H), 7.52 (d, J 16.0, 1H), 7.60 (d, J 8.3, 2H), 7.66 (d, J 8.3, 2H), 7.71 (d, J 8.3, 1H), 7.78 (d, J 8.3, 1H), 7.83 (s, 1H), 8.26 (s, 1H), 9.67 (s, 1H), 12.40 (br s, 1H); MS (ES$^+$) m/z 691 (M+H)$^+$.

EXAMPLE 4

Preparation of (2E)-3-(2-{1-[({3-cyclohexyl-1-[2-(dimethylamino)-2-oxoethyl]-2-phenyl-1H-indol-6-yl}carbonyl)amino]cyclopentyl}-1H-benzimidazol-5-yl)acrylic acid Step 1: Methyl (2E)-3-(4-chloro-3-nitrophenyl)acrylate To a solution of 4-chloro-3-nitrocinnamic acid in a mixture of methanol/DCM (1:1, v/v, 0.09 M), a 2 M solution of trimethylsilyl diazomethane in hexane (4 eq) was slowly added until the yellow color persisted, indicating an excess of diazomethane. The resulting mixture was evaporated. PE was added to the residue and the resultant precipitate was filtered and dried under vacuo to afford the title compound (97%) as a solid. $^1$H NMR (400 MHz; DMSO-$d_6$, 300 K) δ 3.75 (s, 3H), 6.86 (d, J 16, 1H), 7.73 (d, J 16, 1H), 7.84 (d, J 8.4, 1H), 8.08 (d, J 8.4, 1H), 8.48 (s, 1H); MS (ES$^+$) m/z 242 (M+H)$^+$.

Step 2: Preparation of methyl (2E)-3-(4-amino-3-nitrophenyl)acrylate

To a solution of methyl (2E)-3-(4-chloro-3-nitrophenyl)acrylate (from Step 1, 1 eq) in DMSO (0.4 M) at 140° C., ammonia gas was bubbled through for 6 h. The reaction mixture was cooled to RT, degassed with nitrogen, and poured into ice cold water. The precipitate formed was filtered washed with cold water and dried under vacuo to afford the title compound (89%) as a solid. $^1$H-NMR (400 MHz; DMSO-$d_6$, 300 K) δ 3.70, (s, 3H), 6.46 (d, J 16, 1H), 7.04 (d, J 8.8, 1H), 7.60 (d, J 16, 1H), 7.82-7.86 (m, 3H), 8.25 (s, 1H); MS (ES$^-$) m/z 221 (M−H)$^-$.

Step 3: Preparation of methyl (2E)-3-(3,4-diaminophenyl)acrylate

To a solution of methyl (2E)-3-(4-amino-3-nitrophenyl)acrylate (from Step 2, 1 eq) in ethanol (0.2 M) was added tin(II) chloride dihydrate (5.75 eq). The reaction mixture was heated to reflux for 8 h. At this time the reaction was allowed to cool to RT, concentrated and diluted with EtOAc. A saturated aqueous solution of NaHCO$_3$ was added slowly. The mixture was stirred for 20 min; the organic layer was washed with brine, dried over Na$_2$SO$_4$ filtered and evaporated in vacuo. The residue was purified by flash chromatography (SiO$_2$; 70% EtOAc in PE) to afford the title compound (57%). $^1$H-NMR (400 MHz; DMSO-<d$_6$, 300 K) δ 3.67 (s, 3H), 4.59 (s, 2H), 5.17 (s, 2H), 6.08 (d, J 15.6, 1H), 6.5 (d, J 8.0, 1H), 6.74 (d, J 7.6, 1H), 6.82 (s, 1H), 7.39 (d, J 15.6, 1H); MS (ES$^+$) m/z 193 (M+H)$^+$.

Step 4: 1-{5-[(1E)-3-Methoxy-3-oxoprop-1-en-1-yl]-1H-benzimidazol-yl}cyclopentanaminium trifluoroacetate To a solution of methyl (2E)-3-(3,4-diaminophenyl)acrylate (from Step 3.1 eq), 1-[(tert-butoxycarbonyl)amino]cyclopentanecarboxylic acid (1 eq) in DMF (0.02 M), HATU (1 eq) and DIPEA (3 eq) were added. The reaction mixture was left at RT with stirring overnight. The resulting mixture was partitioned between EtOAc and HCl (1 N). The combined EtOAc layers were washed with brine, and the organic phase was dried over Na$_2$SO$_4$, separated, and evaporated in vacuo to afford methyl (2E)-3-{4-[({1-[(tert-butoxycarbonyl)amino]cyclopentyl}carbonyl)amino]phenyl}acrylate, which was used without further purification. MS (ES$^+$) m/z 404 (M+H)$^+$. The foregoing product was dehydrated by heating it at 65° C. in presence of acetic acid. (0.16 M); the reaction residue was purified by RP-HPLC (Conditions Symmetry (Waters) C18 Column, 7 micron, 19×300 mm; flow: 20 mL/min; Gradient: A H$_2$O+0.1% TFA; B: MeCN+0.1% TFA; 70% A isocratic for 2 min., linear to 20% A in 16 min isocratic for 0.5 min. and linear to 10% A for 2 min). Fractions containing pure product were pooled and lyophilized to give methyl (2E)-3-(2-{1-[(tert-butoxycarbonyl)amino]-cyclopentyl}-1H-benzimidazol-5-yl)acrylate. MS (ES$^-$) m/z 384 (M–H)$^-$.

To methyl (2E)-3-(2-{1-[(tert-butoxycarbonyl)amino]cyclopentyl}-1H-benzimidazol-5-yl)acrylate (1 eq) was added a mixture of trifluoroacetic acid and DCM (0.05 M, 1:1, v/v) at RT. The reaction was left at RT for 30 min, then the solvent was evaporated in vacuo to give the title compound as a solid (quantitative). $^1$H NMR (400 MHz; DMSO-d$_6$+TFA, 300 K) δ 1.94 (bs, 4H), 2.10-2.14 (m, 2H), 2.31-2.35 (m, 2H), 3.74 (s, 3H), 6.65 (d, J 16, 1H), 7.63 (d, J 8.1, 1H), 7.68 (d, J 8.1, 1H), 7.83 (d, J 16, 1H), 7.96 (s, 1H), 8.68 (bs, 3H); MS (ES$^+$) m/z 286 (M+H)$^+$.

Step 5: Preparation of (2E)-3-(2-{1-[({3-cyclohexyl-1-[2-(dimethylamino)-2-oxoethyl]-2-phenyl-1H-indol-6-yl}carbonyl)amino]cyclopentyl}-1H-benzimidazol-5-yl)acrylic acid To a solution of 1-{5-[(1E)-3-methoxy-3-oxoprop-1-en-1-yl]-1H-benzimidazol-2-yl}cyclopentanaminium trifluoroacetate (from Step 4, 1 eq), 3-cyclohexyl-1-[2-(dimethylamino)-2-oxoethyl]-2-phenyl-1H-indole-6-carboxylic acid (from Example 1, Step 6, 1 eq) in DMF (0.02 M), HATU (1 eq) and DIPEA (5 eq) were added. The reaction mixture was left at RT with stirring overnight. The resulting mixture was partitioned between EtOAc and hydrochloric acid. The combined EtOAc layers were washed with saturated aqueous NaCl solution, separated, dried over Na$_2$SO$_4$, filtered and evaporated in vacuo to afford methyl (2E)-3-(2-{1-[({3-cyclohexyl-1-[2-(dimethylamino)-2-oxoethyl]-2-phenyl-1H-indol-6-yl}carbonyl)amino]cyclopentyl}-1H-benzimidazol-5-yl)acrylate, which was used without further purification. MS (ES$^+$) m/z 672 (M+H)$^+$.

The foregoing product was dissolved in a mixture THF:MeOH (0.06 M, 1:1, v/v) then LiOH monohydrate (2.5 eq) was added. The reaction mixture was heated at 60° C. for 2 h. HCl (1N) was added to the cooled solution until the pH was acidic and the product was purified by preparative HPLC (Conditions X-Terra (Waters) C18 Column, 5 micron, 19×100 mm; flow: 20 mL/min; Gradient A H$_2$O+0.1% TFA; B: MeCN+0.1% TFA; 70% A isocratic for 2 min., linear to 10% A in 12 min isocratic for 1 min). Fractions containing pure product were pooled and lyophilized to give the title compound (5%). $^1$H-NMR (400 MHz; DMSO-d$_6$, 300 K) δ 1.19-1.31 (m, 3H), 1.65-1.94 (m, 11H), 2.47-2.61 (m, 5H), 2.76 (s, 3H), 2.86 (s, 3H), 4.81 (s, 2H), 6.61 (d, J 16, 1H), 7.32-7.49 (m, 2H), 7.50-7.52 (m, 3H), 7.7-7.85 (m, 6H), 7.96 (s, 1H), 8.98 (s, 1H), 12.5 (bs, 1H); MS (ES$^+$) m/z 658 (M+H)$^+$.

EXAMPLE 5

Preparation of (2E)-3-[4-({[1-({[3-cyclohexyl-1-[2-(dimethylamino)-2-oxoethyl]-2-(6-methoxypyridin-3-yl)-1H-indol-6-yl]carbonyl}ammo)cyclopentyl]-carbonyl}amino) phenyl]acrylic acid Step 1: Preparation of methyl 3-cyclohexyl-1-[2-(dimethylamino)-2-oxoethyl]-2-(6-methoxypyridin-3-yl)-1H-indole-6-carboxylate To a solution of methyl 2-bromo-3-cyclohexyl-1-[2-(dimethylamino)-2-oxoethyl]-1H-indole-6-carboxylate (1 eq), prepared as described in Example 3, Step 1, but using 2-chloro-N,N-dimethylacetamide in the alkylation step, in dioxane (0.06 M) was added bistriphenylphosphine-palladium dichloride (0.2 eq). The reaction mixture was left at RT under nitrogen atmosphere for 15 min, at that rime an aqueous solution of Na$_2$CO$_3$ (2 M), (2.93 eq) and 2-methoxy-5-pyridineboronic acid (2.5 eq) were added. The reaction mixture was heated to reflux for 2 h, then was cooled to RT and concentrated in vacuo. The residue was diluted with DCM, filtered and washed with water, brine, dried over Na$_2$SO$_4$, filtered and evaporated in vacuo to give the title compound (85%). $^1$H NMR (400 MHz; DMSO-d$_6$, 300 K) δ 1.20-1.28 (m, 3H), 1.65-1.85 (m, 7H), 2.50-2.54 (m, 1H), 2.8 (s, 3H), 2.9 (s, 3H), 3.87 (s, 3H), 3.93 (s, 3H), 4.92 (s, 2H), 6.97 (d, J 8.4, 1H), 7.62 (d, J 8.8, 1H), 7.67 (d, J 8.8, 1H), 7.85 (d, J 8.4, 1H), 7.99 (s, 1H), 8.11 (s, 1H); MS (ES$^+$) m/z 450 (M+H)$^+$.

Step 2: Preparation of 3-Cyclohexyl-1-[2-(dimethylamino)-2-oxoethyl]-2-(6-methoxypyridin-3-yl)-1H-indole-6-carboxylic acid Methyl 3-cyclohexyl-1-[2-(dimethylamino)-2-oxoethyl]-2-(6-methoxypyridin-3-yl)-1H-indole-6-carboxylate (from Step 1, 1 eq.) was dissolved in a mixture THF:MeOH (0.07 M, 1:1, v/v) then an aqueous solution of LiOH monohydrate (3 eq, 0.21 M) was added. The reaction mixture was heated at 60° C. for 4 h. It was allowed to cool to RT, and then hydrochloric acid was added. The precipitate that formed was collected by filtration and dried in vacuo to give the title compound (90%). $^1$H NMR (400 MHz; DMSO-d$_6$, 300 K) δ 1.17-1.28 (m, 3H), 1.65-1.86 (m, 7H), 2.45-2.55 (m, 1H), 2.8 (s, 3H), 2.96 (s, 3H), 3.94 (s, 3H), 4.91 (s, 2H), 6.97 (d, J 8.4, 1H), 7.62 (d, J 8.8, 1H), 7.65 (d, J 8.8, 1H), 7.82 (d, J 8.4, 1H), 7.95 (s, 1H), 8.11 (s, 1H), 12.6 (bs, 1H); MS (ES$^+$) m/z 436 (M+H)$^+$.

Step 3: (2E)-3-[4-({[1-({[3-Cyclohexyl-1-[2-(dimethylamino)-2-oxoethyl]-2-(6-methoxypyridin-3-yl)-1H-indol-6-yl]carbonyl}amino)cyclopentyl]carbonyl}amino) phenyl]acrylic acid Following the procedure from Example 1, Step 8, the title compound was obtained as a colorless solid after lyophilzation. $^1$H NMR (400 MHz; DMSO-d$_6$, 300 K) δ 1.24-1.27 (m, 3H), 1.69-1.83 (m, 11H), 1.86-2.09 (m, 2H), 2.1-2.34 (m, 2H), 2.5-2.54 (m, 1H), 2.77 (s, 3H), 2.94 (s, 3H), 3.93 (s, 3H), 4.88 (s, 2H), 6.39 (d, J 16, 1H), 6.96 (d, J 8.4, 1H), 7.5 (d, J 16, 1H), 7.57-7.65 (m, 5H), 7.71 (d, J 8.4, 1H), 7.79 (d, J 8.4, 1H), 7.87 (s, 1H), 8.1-8.11 (d, J 4, 1H), 8.27 (s, 1H), 9.66 (s, 1H); MS (ES$^+$) m/z 692 (M+H)$^+$.

EXAMPLE 6

Preparation of (2E)-3-[4-({[1-({[3-cyclohexyl-1-[2-(dimethylamino)-2-oxoethyl]-2-(1,3-oxazol-5-yl)-1H-indol-6-yl]carbonyl}amino)cyclopentyl]carbonyl}amino)phenyl]acrylic acid Step 1: methyl 3-cyclohexyl-2-vinyl-1H-indole-6-carboxylate To a solution of methyl 2-bromo-3-cyclohexyl-1H-indole-6-carboxylate (from Example 1, Step 3) in dioxane (0.15 M) was added tri-n-butyl vinyl tin (1.1 eq.) followed by bis(triphenylphosphine)palladium(II) chloride (0.1 eq.). The reaction was stirred under nitrogen at 100° C. for 3 h and then cooled to RT. The mixture was then diluted with EtOAc and washed with brine (3×). The organic phase was then dried over Na$_2$SO$_4$ and evaporated to dryness. The residual material was purified by chromatography on silica gel (PE:EtOAc, 9:1). The product fractions were evaporated and the residual material re-crystallised from DCM with PE. The product was obtained as yellow crystalline material (60%).

$^1$H NMR (400 MHz, DMSO-d$_6$, 300 K) δ, 1.37-1.45 (m, 3H); 1.66-1.90 (2m, 7H); 2.87-2.93 (m, 1H); 3.84 (s, 3H); 5.36 (d, J 11.6, 1H); 5.83 (d, J 17.3, 1H); 6.92-6.99 (dd, J$_a$ 11.6, J$_b$ 17.5, 1H); 7.53 (d, J 8.5, 1H); 7.74 (d, J 8.5, 1H); 7.93 (s, 1H); 11.4 (s, 1H). MS (ES$^+$) m/z 2845 (M+H)$^+$.

Step 2: methyl 3-cyclohexyl-1-[2-(dimethylamino)-2-oxoethyl]-2-vinyl-1H-indole-6-carboxylate To a solution of methyl 3-cyclohexyl-2-vinyl-1H-indole-6-carboxylate (from Step 1) in DMF, NaH (1.2 eq.; 60% in mineral oil) was added. After evolution of gas had ceased, N,N-dimethyl chloroacetamide (1.3 eq.) was added dropwise. The mixture was stirred overnight, then all volatiles were evaporated and the residual material was taken up in DCM. The solution was washed with 1N HCl (1×), brine (2×) and then dried over Na$_2$SO$_4$. The solvent was evaporated and the residual material crystallised from DCM with PE. The product was obtained as a yellow solid (68%). $^1$H NMR (400 MHz, DMSO-d$_6$, 300 K) δ 1.36-1.38 (m, 3H); 1.69-1.96 (3m, 7H); 2.85 (s, 3H); 2.91-2.95 (m, 1H); 3.13 (s, 3H); 3.85 (s, 3H); 5.15 (s, 2H); 5.41 (d, J 17.8, 1H); 5.61 (d, J 11.6, 1H); 6.71-6.78 (dd, J$_a$ 11.6, J$_b$ 17.8, 1H); 7.61 (d, J 78.3, 1H); 7.81 (d, J 8.5, 1H); 7.94 (s, 1H). MS (ES$^+$) m/z 369.6 (M+H)$^+$.

Step 3: methyl 3-cyclohexyl-2-(1,2-dihydroxyethyl)-1-[2-(dimethylamino)-2-oxoethyl]-1H-indole-6-carboxylate To a solution of methyl 3-cyclohexyl-1-[2-(dimethylamino)-2-oxoethyl]-2-vinyl-1H-indole-6-carboxylate (from Step 2) in THF/acetone (0.2 M, 1:1, v:v) was added N-methyl morpholine N-oxide (1.2 eq.). To the resulting suspension water was added (1 volume part), followed by a solution of osmium tetroxide in water (0.1 eq., 4% solution). The resulting solution was left stirring overnight at RT. After one night a saturated solution of sodium sulfite in water was added and the mixture was left stirring for 30 min. The solution was diluted with water and extracted with DCM (3×) and EtOAc (2×). The combined organic extracts were dried over Na$_2$SO$_4$ and evaporated in vacuo. The residual material was dissolved in DCM and precipitated with PE. The product was obtained as a greyish foam (91%).

$^1$H NMR (400 MHz, DMSO-d$_6$, 300 K) δ 1.25-1.37 (m, 3H); 1.73-1.89 (m, 7H); 2.86 (s, 3H); 2.92-2.95 (m, 1H); 3.14 (s, 3H); 3.37-3.42 (m, 1H); 3.53-3.58 (m, 1H); 3.83 (s, 3H); 4.78-4.81 (m, 1H); 4.96-4.98 (m, 1H); 5.30 (d, J 17.5, 1H); 5.42 (d, J 17.5, 1H); 5.59 (d, J 3.7, 1H); 7.57 (d, J 8.3, 1H); 7.75 (d, J 8.3, 1H); 7.84 (s, 1H). MS (ES$^+$) m/z 425.6 (M+Na)$^+$.

Step 4: methyl 3-cyclohexyl-1-[2-(dimethylamino)-2-oxoethyl]-2-formyl-1H-indole-6-carboxylate To a solution of methyl 3-cyclohexyl-2-(1,2-dihydroxyethyl)-1-[2-(dimethylamino)-2-oxoethyl]-1H-indole-6-carboxylate (from Step 3) in THF/water (0.05 M, 1:1, v:v) cooled to 0° C. was added sodium periodate (1.2 eq.). The resulting mixture was allowed to warm to RT and left stirring for a further 3 h. The mixture was diluted with EtOAc and 5% aq. citric acid solution. The phases were separated and the aqueous phase was extracted with EtOAc. The combined organic phases were extracted with aqueous citric acid (2% solution), sat. aq. NaHCO$_3$ solution and brine. The organic phase was then dried over Na$_2$SO$_4$ and evaporated in vacuo. The residual material was then crystallised from EtOAc with PE. The product was obtained as an off-white solid (83%).

$^1$H NMR (400 MHz, DMSO-d$_6$, 300 K) δ 1.43-1.48 (m, 3H); 1.65-1.98 (3m, 7H); 2.84 (s, 3H); 3.15 (s, 3H); 3.44-3.50 (m, 1H); 3.88 (s, 3H); 5.51 (s, 2H); 7.66 (d, J 8.6, 1H); 8.07 (d, J 8.7, 1H); 8.17 (s, 1H); 10.20 (s, 1H). MS (ES$^+$) m/z 371.6 (M+H)$^+$.

Step 5: methyl 3-cyclohexyl-1-[2-(dimethylamino)-2-oxoethyl]-2-(1,3-oxazol-5-yl)-1H-indole-6-carboxylate To a solution of methyl 3-cyclohexyl-1-[2-(dimethylamino)-2-oxoethyl]-2-formyl-1H-indole-6-carboxylate (from Step 4) in MeOH (0.05 M) was added K$_2$CO$_3$ (1.05 eq.) and tosylmethyl isocyanide (1.05 eq.). The resulting solution was refluxed under nitrogen for 1.5 h. The mixture was diluted with EtOAc and the organic phase was extracted with HCl (1N) and brine. The organic phase was then dried over Na$_2$SO$_4$ and evaporated in vacuo to give the clean product (quantitative).

$^1$H NMR (400 MHz, DMSO-d$_6$, 300 K) δ 1.21-1.38 (m, 3H); 1.65-1.98 (m, 7H); 2.84 (s, 3H); 3.08 (s, 3H); 3.88 (s, 3H); 5.15 (s, 2H); 7.31 (s, 1H); 7.66 (d, J 8.6, 1H); 7.91 (d, J 8.7, 1H); 8.08 (s, 1H); 8.6 (s, 1H). MS (ES$^+$) m/z 410.5 (M+H)$^+$.

Step 6: 3-cyclohexyl-1-[2-(dimethylamino)-2-oxoethyl]-2-(1,3-oxazol-5-yl)-1H-indole-6-carboxylic acid To a solution of methyl 3-cyclohexyl-1-[2-(dimethylamino)-2-oxoethyl]-2-(1,3-oxazol-5-yl)-1H-indole-6-carboxylate (from Step 5) in MeOH/THF/H$_2$O (0.05 M, 1:1:1, v:v:v) was added KOH (5 eq.). The resulting solution was stirred at RT overnight. The reaction mixture was diluted with EtOAc, then washed with hydrochloric acid (1N), brine, and dried over Na$_2$SO$_4$. Evaporation gave an off-white foam, which was purified by RP-HPLC (column: Waters X-terra C18, 19×150 mm, 5 micron; flow 20 mL/min) to give the title compound as a white powder after lyophilization (53%).

$^1$H NMR (400 MHz, DMSO-d$_6$, 300 K) δ 1.21-1.38 (m, 3H); 1.65-1.98 (m, 7H); 2.84 (s, 3H); 3.08 (s, 3H); 5.15 (s, 2H); 7.35 (s, 1H); 7.66 (d, J 8.6, 1H); 7.91 (d, J 8.7, 1H); 8.08 (s, 1H); 8.6 (s, 1H). MS (ES$^+$) m/z 396.56 (M+H)$^+$.

Step 7: (2E)-3-[4-({[1-({[3-cyclohexyl-1-[2-(dimethylamino)-2-oxoethyl]-2-(1,3-oxazol-5-yl)-1H-indol-6-yl]carbonyl}amino)cyclopentyl]carbonyl}amino)phenyl]acrylic acid A solution (0.04 M) of 3-cyclohexyl-1-[2-(dimethylamino)-2-oxoethyl]-2-(1,3-oxazol-5-yl)-1H-indole-6-carboxylic acid (from Step 6) in DMF was treated with DIPEA (3 eq.), HATU (2 eq.) and ethyl (2E)-3-(4-{[(1-aminocyclopentyl)carbonyl]amino}phenyl)acrylate (from Example 1, Step 7, 1.1 eq.). The solution was stirred at 25° C. for 12 h and then evaporated in vacuo. The residual material was purified by chromatography on silica gel (PE:EtOAc, 8:2, then EtOAc: PE 9:1). The product fractions were evaporated and the material obtained was then dissolved in THF/MeOH (1:1). The resulting solution was treated with LiOH monohydrate (3 eq.) and stirred at RT overnight. The product was isolated by preparative HPLC (stationary phase: Waters Xterra C18 19×150 mm, 5 micron; flow 20 mL/min). After lyophilisation the product was obtained as a colourless amorphous solid (98%).

$^1$H NMR (400 MHz, DMSO-d$_6$, 300K) δ 1.23-1.34 (m, 3H); 1.68-1.87 (m, 11H); 2.06-2.09 (m, 2H); 2.31-2.33 (m, 2H); 2.80 (m, 4H); 3.05 (s, 3H); 5.08 (s, 2H); 6.38 (d, J 15.8, 1H); 7.33 (s, 1H); 7.49 (d, J 15.8, 1H); 7.57 (d, J 8.6, 2H); 7.63 (d, J 8.6, 2H); 7.70 (d, J 8.3, 1H); 7.84 (d, J 8.3, 1H); 7.95 (s, 1H); 8.30 (s, 1H); 8.59 (s, 1H); 9.66 (s, 1H). MS (ES$^+$) m/z 652.7 (M+H)$^+$.

EXAMPLE 7

Preparation of (2E)-3-{4-[({1-[({3-Cyclohexyl-1-[2-(dimethylamino)-2-oxoethyl]-2-cyclopropyl-1H-indol-6-yl}carbonyl)amino]cyclopentyl}carbonyl)amino]phenyl}-acrylic acid Step 1: Methyl 3-cyclohexyl-2-cyclopropyl-1-[2-(dimethylamino)-2-oxoethyl]-1H-indole-6-carboxylate To a solution of methyl 2-bromo-3-cyclohexyl-1-[2-(dimethylamino)-2-oxoethyl]-1H-indole-6-carboxylate (prepared as in published International patent application WO2004/087714) in toluene (0.24 M) was added cyclopropylboronic acid (1.3 eq.) followed by potassium phosphate (3.5 eq.). The mixture was degassed, then Pd(OAc)$_2$ (0.1 eq.) and tricyclohexylphosphine (0.2 eq.) were added. The reaction was stirred under nitrogen at 100° C. for 1.5 h and then cooled to RT. EtOAc was added and the organic phase was washed with water and brine, dried over NaSO$_4$ and evaporated in vacuo to leave a residue which was purified by flash chromatography (PE/EtOAc 1/1) to give the title compound (70%).

$^1$H NMR (300 MHz, CDCl$_3$, 300 K) δ 0.91-0.98 (m, 2H), 1.21-1.28 (m, 2H), 1.48-1.75 (m, 3H), 1.92-2.25 (m, 9H), 3.23 (s, 3H), 3.40 (s, 3H), 4.14 (s, 3H), 5.31 (s, 2H), 7.90 (m, 2H), 8.05 (s; 1H). MS (ES$^+$) m/z 383 (M+H)$^+$.

Step 2: (2E)-3-{4-[({1-[({3-Cyclohexyl-1-[2-(dimethylamino)-2-oxoethyl]-2-cyclopropyl-1H-indol-6-yl}carbonyl)amino]cyclopentyl}carbonyl)amino]phenyl}-acrylic acid Methyl 3-cyclohexyl-2-cyclopropyl-1-[2-(dimethylamino)-2-oxoethyl]-1H-indole-6-carboxylate (from Step 1) was dissolved in DCM (0.2 M). Boron tribromide (1.0 M solution in DCM, 2.0 eq.) was added at 0° C. and the resultant solution stirred for 2 h at RT. The solvent was removed in vacuo and the residue taken into MeCN and treated with HCl (1N). The solvents were removed to give the acid as a white solid, which was dissolved in DMF (0.1 M) and treated with ethyl (2E)-3-(4-{[(1-aminocyclopentyl)carbonyl]amino}phenyl)acrylate (from Example 1, Step 7, 1.1 eq.), HATU (1.5 eq.), and DIPEA (4 eq.) and the solution was stirred overnight at RT. The solution was diluted with EtOAc and washed with HCl (1N), water and brine, dried over Na$_2$SO$_4$ and evaporated in vacuo to leave a residue which dissolved in THF/MeOH/H$_2$O (4/1/1, v/v/v) was treated with LiOH overnight. Solvents were then removed in vacuo, the residue acidified with HCl (1N) and dissolved in MeCN and purified by RP-HPLC (column: Waters X-terra C18, 19×150 mm, 5 micron; flow 20 mL/min) to give the title compound as a white powder after lyophilization (55%). $^1$H NMR (400 MHz, DMSO-d$_6$, 300 K) δ 0.56-0.57 (m, 2H), 0.97-0.99 (m, 2H), 1.35-1.41 (m, 3H), 1.65-1.94 (m, 12H), 2.03-2.08 (m, 2H), 2.29-2.35 (m, 2H), 2.86 (s, 3H), 3.02-3.08 (m, 1H), 3.17 (s, 3H), 5.18 (s, 2H), 6.36-6.40 (d, J 16, 1H), 7.47-7.51 (d, J 16, 1H), 7.56-7.67 (m, 6H), 7.76 (s, 1H), 8.17 (s, 1H), 9.63 (s, 1H); MS (ES$^+$) m/z 626 (M+H)$^+$.

EXAMPLE 8

(2E)-3-{4-[({1-[({3-cyclohexyl-1-[2-(4-methylpiperazin-1-yl)-2-oxoethyl]-2-phenyl-1H-indol-6-yl}carbonyl)amino]cyclopentyl}carbonyl) amino]phenyl}acrylic acid

Step 1: tert-butyl 3-cyclohexyl-1H-indole-6-carboxylate

A solution of 3-cyclohexenyl-1H-indole-6-carboxylic acid (1 eq., prepared as described in Example 1, Step 1) in dry DCM (0.19 M) was treated with tert-butyl N,N'-diisopropylimidocarbamate (2 eq.). The resulting clear solution was heated at reflux for 36 h. Addition of a further equivalent of isourea was required after 16 h to drive the reaction to completion. After cooling down the solvent was evaporated giving a residue that was purified by silica gel chromatography (Flashmaster Personal, PE:EtOAc, 30:1) affording tert-butyl 3-cyclohexyl-1H-indole-6-carboxylate (75%) $^1$H NMR (300 MHz, DMSO-$d_6$, 300 K) δ 1.22-1.53 (m, 5H), 1.54 (s, 9H), 1.70-1.86 (m, 3H), 1.95-1.98 (m, 2H), 2.69-2.86 (m, 1H), 7.29 (s, 1H), 7.49-7.57 (m, 2H), 7.93 (s, 1H), 11.09 (s, 1H); MS (ES$^+$) m/z 300 (M+H)$^+$.

Step 2: tert-butyl 2-bromo-3-cyclohexyl-1H-indole-6-carboxylate

To a solution (0.14 M) of tert-butyl-3-cyclohexyl-1H-indole-6-carboxylate in CCl$_4$ was added NBS (1.1 eq.) portionwise over a period of 1 h at RT. The resulting mixture was stirred 2 h at RT, then a saturated aqueous solution of sodium thiosulfate was added and the reaction mixture vigorously stirred for 1 h. EtOAc was then added and the organic layer was separated and washed with a saturated aqueous solution of sodium thiosulfate (3×) then dried over Na$_2$SO$_4$ and evaporated. The residue was purified by silica gel chromatography (Flashmaster Personal, petroleum ether:EtOAc, 20:1) to give the title compound (68%) as a solid. $^1$H NMR (300 MHz, DMSO-$d_6$, 300 K) δ 1.33-1.39 (m, 3H), 1.54 (s, 9H), 1.65-1.99 (m, 7H), 2.73-2.81 (m, 1H), 7.52 (d, J 7.6, 1H), 7.70 (d, J 77.6, 1H), 7.83 (s, 1H), 11.92 (br s, 1H); MS (ES$^+$) m/z 379 (M+H)$^+$.

Step 3: tert-butyl 3-cyclohexyl-2-phenyl-1H-indole-6-carboxylate

To a solution of tert-butyl 2-bromo-3-cyclohexyl-1H-indole-6-carboxylate (from Step 2) in DME and EtOH (0.2 M, 3:1, v/v) was added phenyl-boronic acid (1.2 eq.) followed by 2 M aqueous Na$_2$CO$_3$ (8.5 eq.). The mixture was degassed with argon, then Pd(PPh$_3$)$_4$ (0.1 eq.) was added and the mixture stirred under argon at 80° C. for 1 h. After cooling to RT, EtOAc was added and the organic layer washed with HCl solution (1N, ×2) and brine. The organic layer was dried over Na$_2$SO$_4$ and evaporated and the residue purified by silica gel chromatography (Flashmaster Personal, PE:EtOAc, 20:1) to give the title compound (90%). $^1$H NMR (400 MHz, DMSO-$d_6$, 300 K) δ 1.21-1.48 (m, 3H), 1.56 (s, 9H), 1.65-1.80 (m, 5H), 1.90-2.05 (m, 2H), 2.79-2.95 (m, 1H), 7.50-7.57 (m, 6H), 7.40-7.50 (m, 1H), 7.79 (d, J 7.6, 1H), 7.94 (s, 1H); MS (ES$^+$) m/z 376 (M+H)$^+$.

Step 4: 3-cyclohexyl-1-[2-(4-methylpiperazin-1-yl)-2-oxoethyl]-2-phenyl-1H-indole-6-carboxylic acid Tert-Butyl 3-cyclohexyl-2-phenyl-1H-indole-6-carboxylate (from Step 3) was dissolved in DMF (0.18 M). NaH (60% suspension in mineral oil, 1.5 eq.) was added and the resultant mixture stirred for 30 min at RT. Neat methyl bromoacetate (1.5 eq.) was added dropwise. After 1 h, analytical RP HPLC indicated complete conversion of the starting material. The mixture was diluted with EtOAc, and then washed with water (3×) and brine. Drying over Na$_2$SO$_4$ and evaporation gave a residue which was dissolved in THF/H$_2$O (0.17 M, 4:1 v/v) and treated with LiOH monohydrate (1.3 eq) for 4 h at RT. The reaction mixture was acidified with HCl (1N) and extracted into EtOAc. The organic layer was washed with brine, dried over Na$_2$SO$_4$ and evaporated. The crude material (>90% pure by analytical HPLC) was dissolved in dry DMF (0.1 M), treated with DIPEA (3 eq.), HATU (2 eq) and N-methyl piperazine (1.5 eq) and the resulting solution was stirred overnight at RT.

The reaction mixture was extracted into EtOAc and the organic layer washed with HCl (2×, 1N), saturated aqueous NaHCO$_3$ (×2) and with brine. The residue obtained by drying and evaporation of the organic layer was treated with TFA/DCM (0.05 M, 1:1 v/v) for 1.5 h at RT. Evaporation of the volatiles afforded the trifluoroacetate salt of the title compound as yellow foam (60%).

$^1$H NMR (400 MHz, DMSO-$d_6$, 300K) δ1.17-1.35 (3H, m), 1.63-1.73 (5H, m), 1.80-1.89 (2H, m), 2.53-2.60 (1H, m), 2.81 (3H, s), 2.70-2.97 (4H, m), 3.18-3.42 (2H, m), 3.97-4.11 (1H, m), 4.31-4.40 (1H, m), 4.94 (1H, s), 5.02 (1H, s), 7.30 (2H, d, J 6.8), 7.50-7.55 (3H, m), 7.66 (1H d, J 8.4), 7.83 (1H, d, J 8.4), 7.98 (1H, s), 9.88 (1H, bs), 12.50 (1H, bs). MS (ES$^+$) m/z 460 (M+H)$^+$.

Step 5: (2E)-3-{4-[({1-[({3-cyclohexyl-1-[2-(4-methylpiperazin-1-yl)-2-oxoethyl]-2-phenyl-1H-indol-6-yl}carbonyl)amino]cyclopentyl}carbonyl)amino]phenyl}acrylic acid A solution of 3-cyclohexyl-1-[2-(4-methylpiperazin-1-yl)-2-oxoethyl]-2-phenyl-1H-indole-6-carboxylic acid (from Step 4) in DMF (0.1 M) was treated with DIPEA (4 eq.), HATU (1.5 eq.) and ethyl (2E)-3-(4-{[(1-aminocyclopentyl)carbonyl]amino}phenyl)acrylate (1.1 eq, prepared as described in Example 1, Step 7). The solution was stirred at 25° C. overnight. The mixture was diluted with EtOAc, and then washed sequentially with HCl (2×, 1N), saturated aqueous NaHCO$_3$ (2×) and brine. The organic layer was dried over Na$_2$SO$_4$ and concentrated to afford an oil, which was dissolved in a mixture of THF/MeOH/H$_2$O (0.05 M, 4:1:1, v/v/v). LiOH monohydrate (1.3 eq.) was added and the resultant mixture stirred at 40° C. for 5 h. The reaction mixture was acidified with HCl (1N) and purified by RP-HPLC (column: Waters X-terra C18, 19×150 mm, 5 micron; flow 17 mL/min) to give the title compound (20%) as a white powder after lyophilization.

$^1$H NMR (400 MHz, DMSO-$d_6$, 340 K) δ 1.11-1.27 (m, 3H), 1.68-1.87 (m, 11H), 2.03-2.16 (m, 2H), 2.30-2.38 (m, 2H), 2.60-2.62 (m, 1H), 2.80 (s, 3H), 2.90-3.40 (m, 8H, partially shielded by water), 4.94 (s, 2H), 6.37 (d, J 16.0, 1H), 7.32 (d, J 6.4, 2H), 7.46-7.55 (m, 4H), 7.59 (d, J 8.4, 2H), 7.65 (d, J 8.4, 2H), 7.71 (d, J 8.2, 1H), 7.80 (d, J 8.2, 1H), 7.86 (s, 1H), 8.12 (s, 1H), 9.52 (s, 1H), 12.1 (bs, 1H). MS (ES+) m/z 716 (M+H)$^+$.

Table 1 contains further examples.

TABLE 1
| No. | Structure | MS (M + H)+ |
|---|---|---|
| 1 | 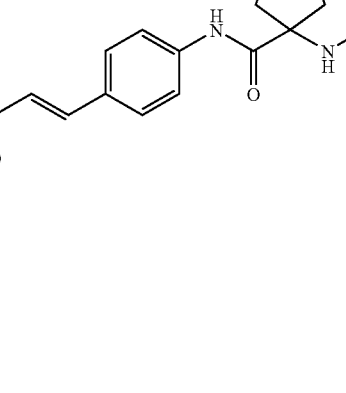 | 675 |
| 2 | 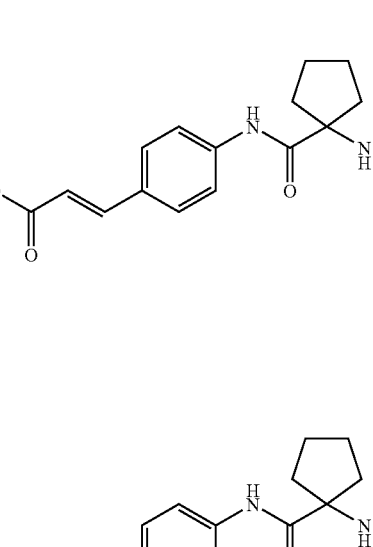 | 758 |
| 3 | 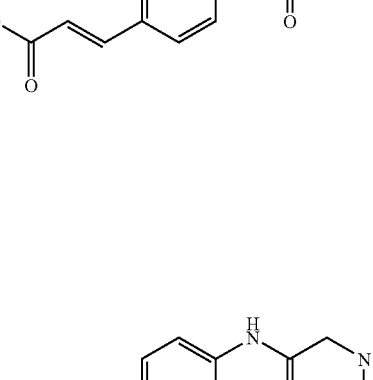 | 696 |
| 4 | 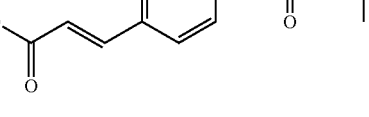 | 621 |

TABLE 1-continued
| No. | Structure | MS (M + H)+ |
|---|---|---|
| 5 | 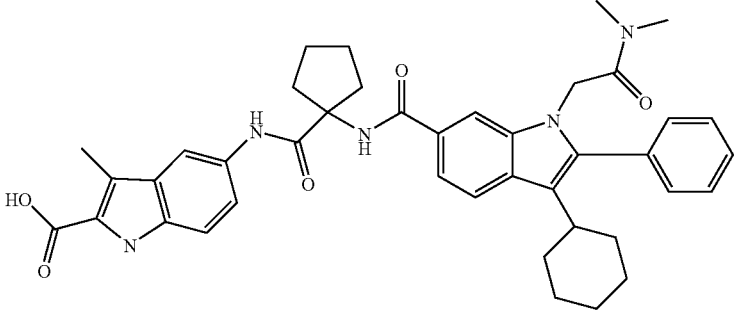 | 705 |
| 6 | 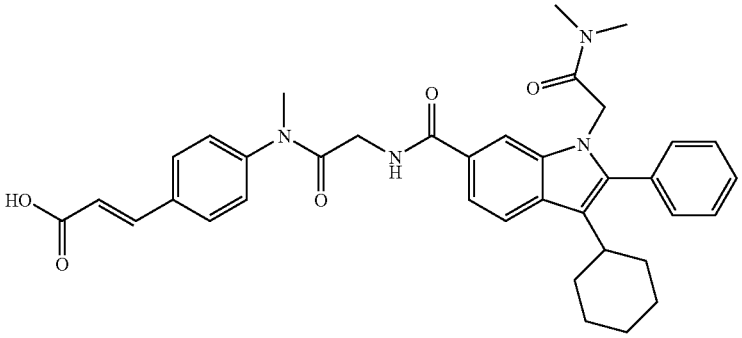 | 621 |
| 7 | 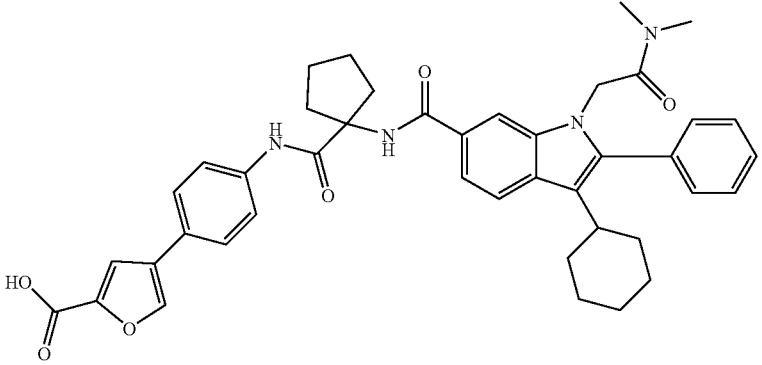 | 701 |
| 8 | 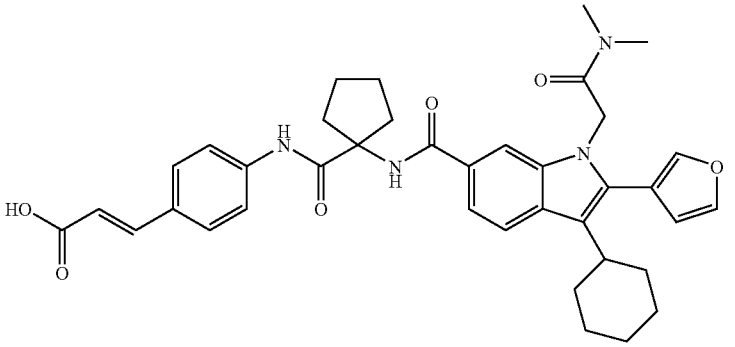 | 651 |

TABLE 1-continued
| No. | Structure | MS (M + H)+ |
|---|---|---|
| 9 | 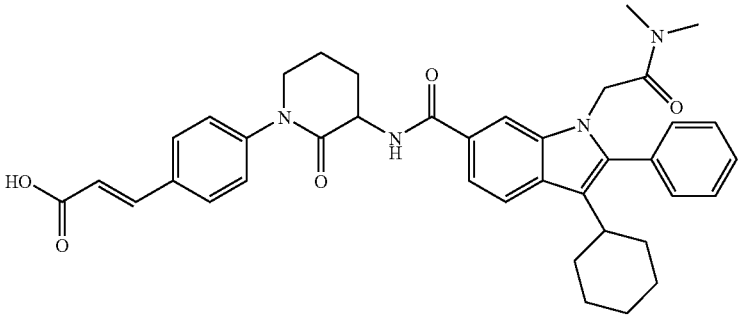 | 647 |
| 10 | 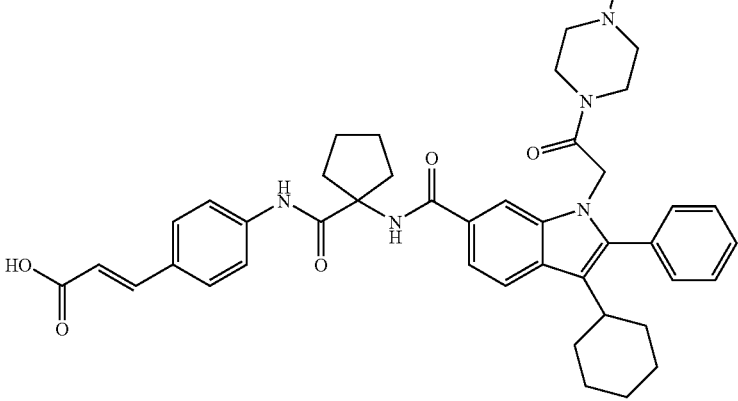 | 716 |
| 11 | 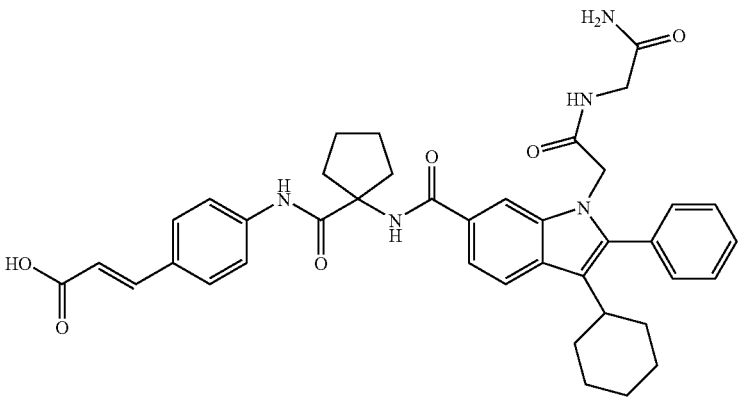 | 690 |
| 12 | 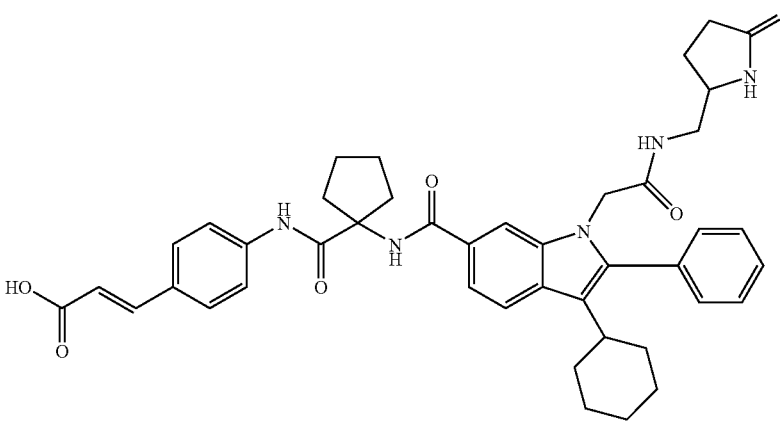 | 730 |

TABLE 1-continued

| No. | Structure | MS (M + H)+ |
|---|---|---|
| 13 | 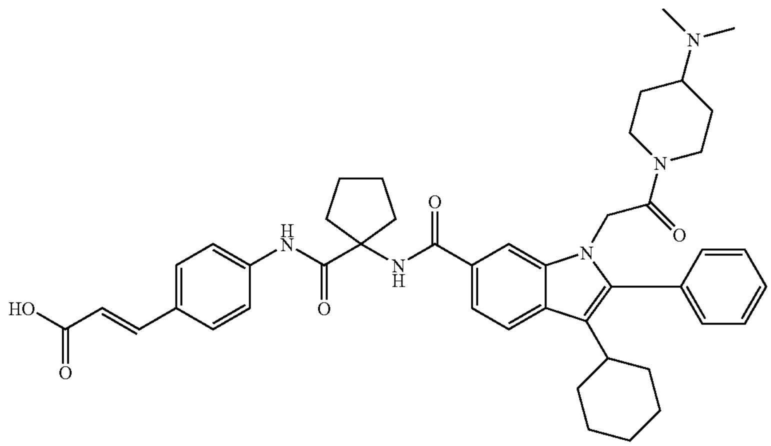 | 744 |
| 14 | 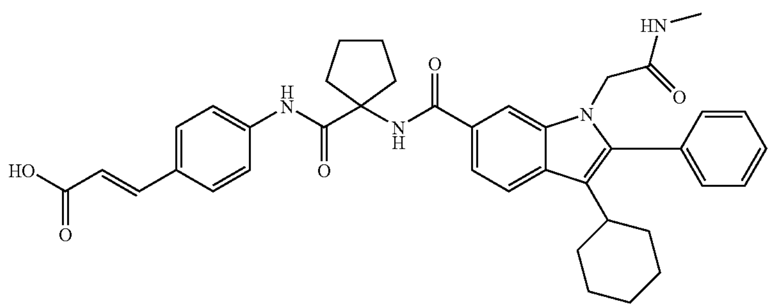 | 647 |
| 15 | 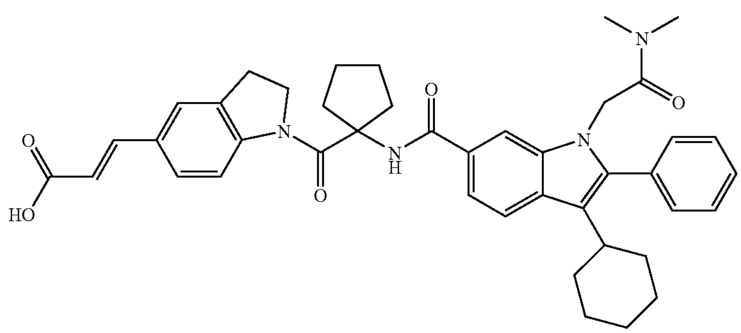 | 687 |
| 16 | 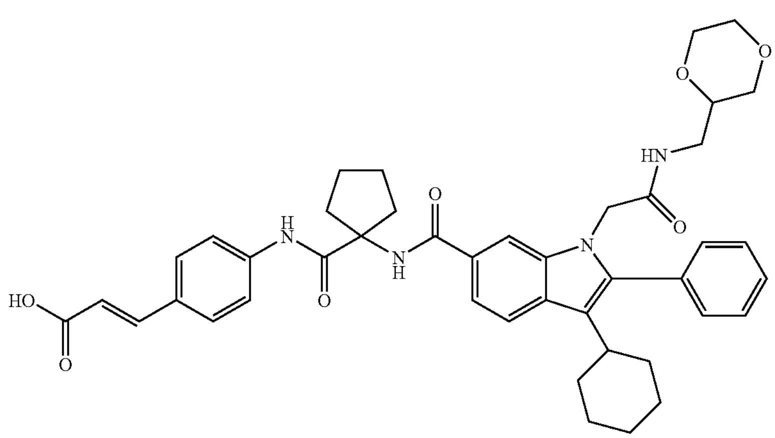 | 733 |

TABLE 1-continued

| No. | Structure | MS (M + H)+ |
|---|---|---|
| 17 | 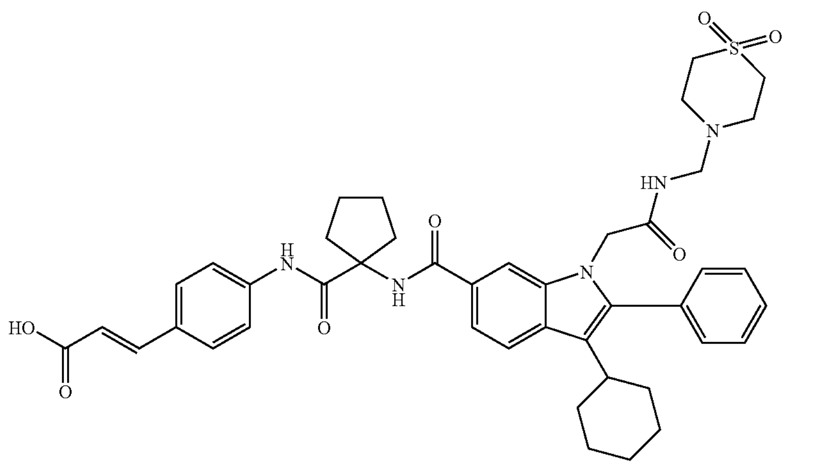 | 751 |
| 18 | 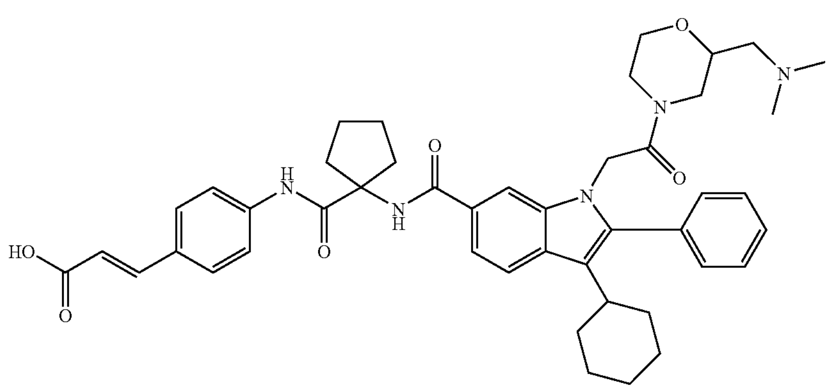 | 761 |
| 19 | 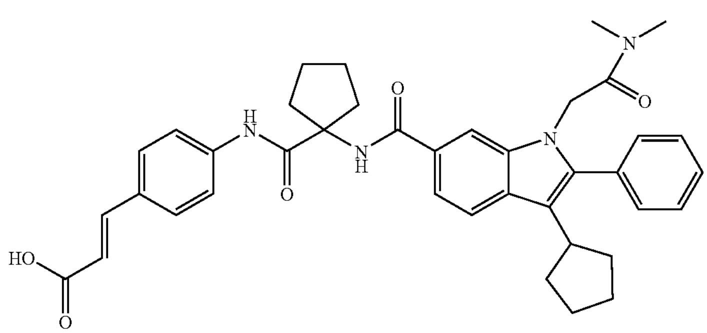 | 647 |

TABLE 1-continued

| No. | Structure | MS (M + H)+ |
|---|---|---|
| 20 | 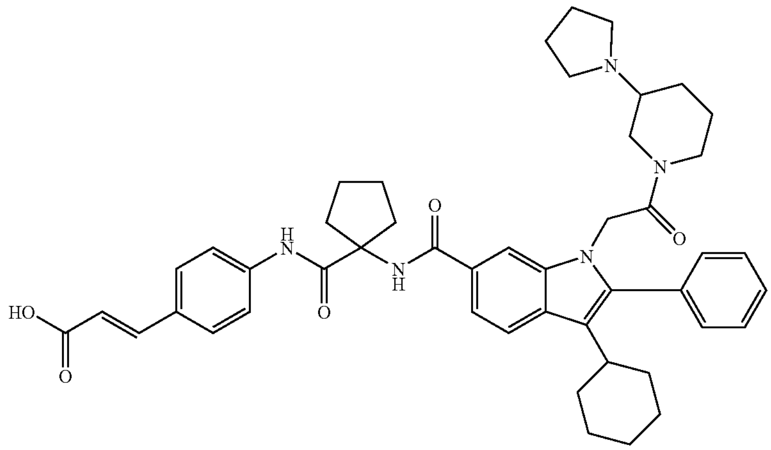 | 771 |
| 21 | 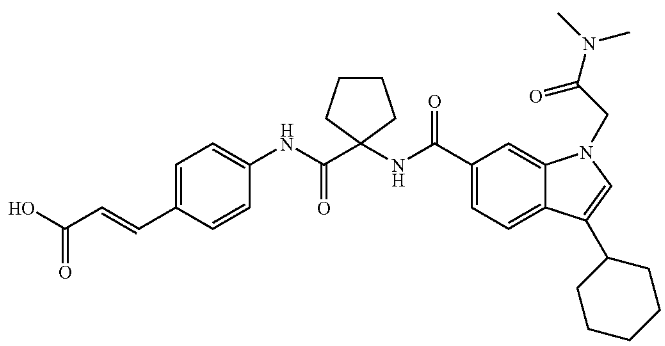 | 585 |
| 22 | 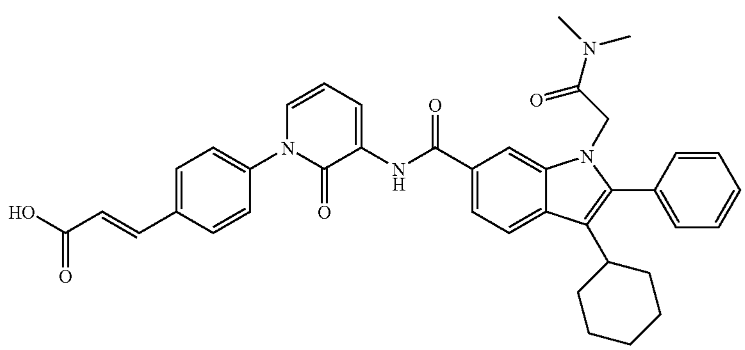 | 643 |
| 23 | 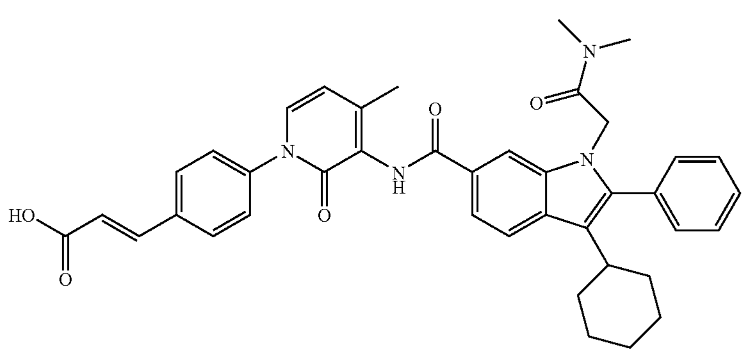 | 657 |

TABLE 1-continued

| No. | Structure | MS (M + H)+ |
| --- | --- | --- |
| 24 | 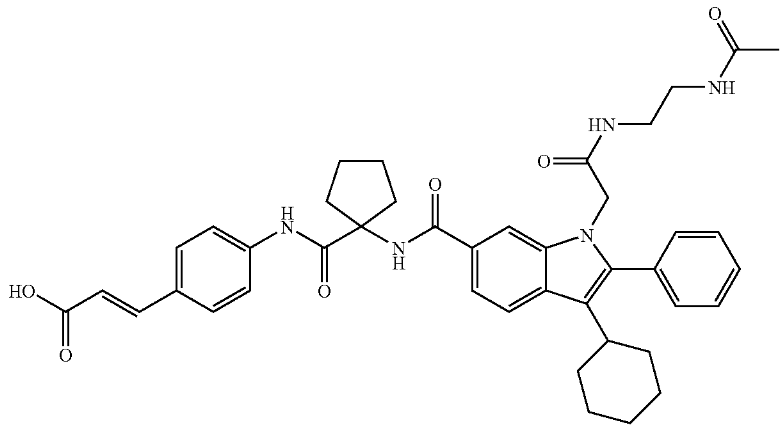 | 718 |
| 25 | 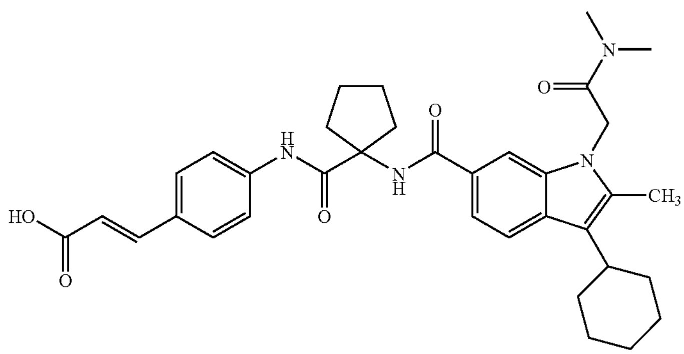 | 599.4 |
| 26 | 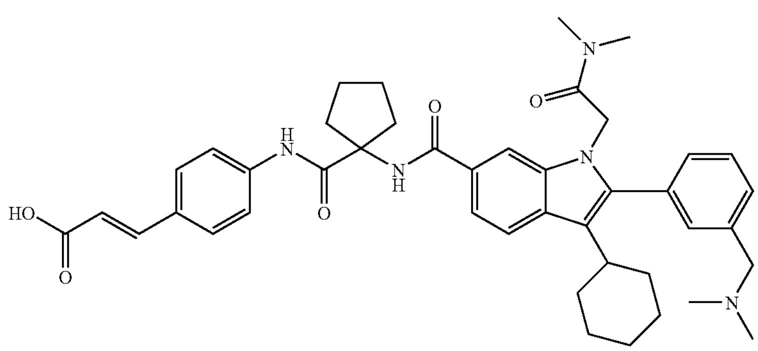 | 718.7 |
| 27 | 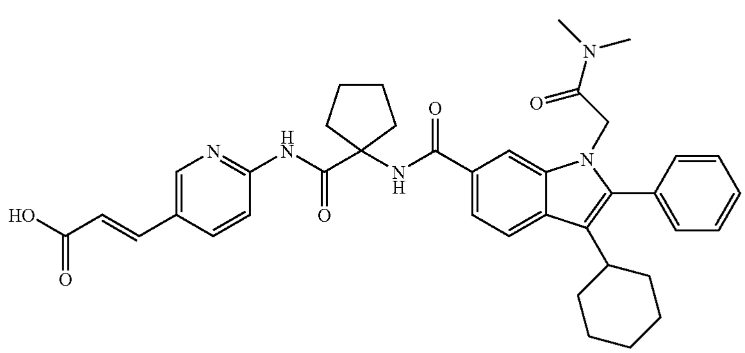 | 662.6 |

TABLE 1-continued

| No. | Structure | MS (M + H)+ |
|---|---|---|
| 28 | 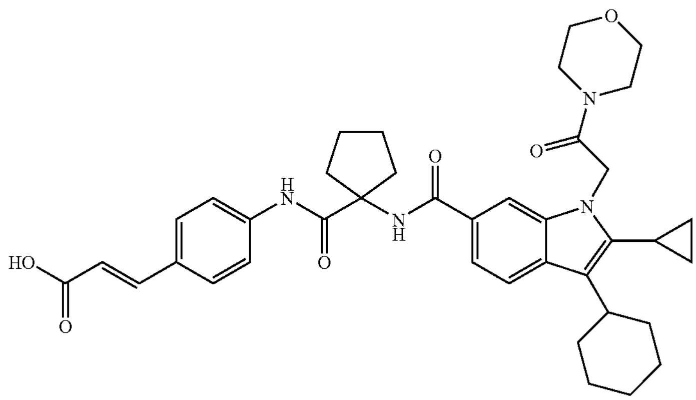 | 667.7 |
| 29 | 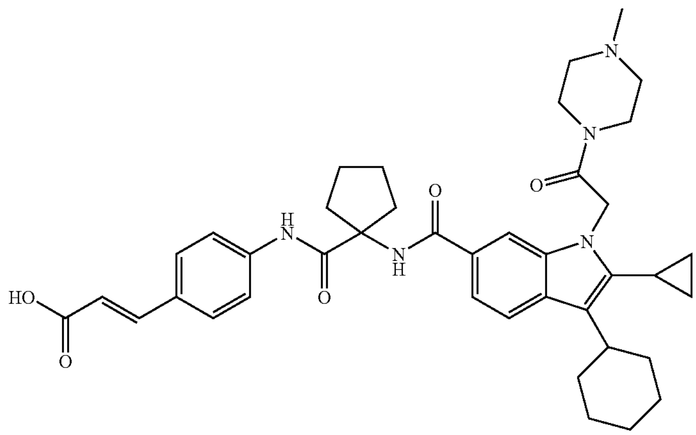 | 680.8 |

The invention claimed is:

1. A compound of the formula (Ia) or a pharmaceutically acceptable salt thereof:

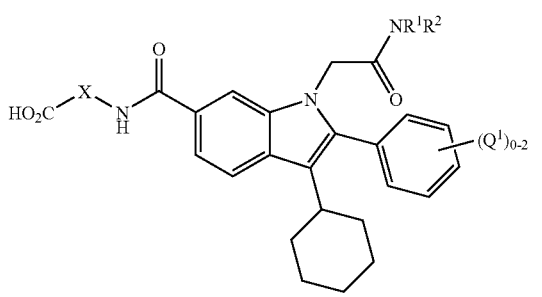

(Ia)

wherein:

Q[1] is halogen, hydroxy, $C_{1-4}$alkyl, $C_{1-4}$alkoxy, aryl, heteroaryl, $CONR^aR^b$, $C_nH_{2n}NR^aR^b$, $-O-(CH_2)_{2-4}R^aR^b$, $-O-C_nH_{2n}CONR^aR^b$, $-O-C_nH_{2n}$aryl, $-O-C_nH_{2n}$heteroaryl, or $-O-CHR^cR^d$;

$R^a$ and $R^b$ are each independently selected from hydrogen, $C_{1-4}$-alkyl or $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

n is 0, 1, 2 or 3;

$R^c$ and $R^d$ are each independently selected from hydrogen or $C_{1-4}$alkoxy;

or $R^c$ and $R^d$ are linked by a heteroatom selected from N, O or S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$R^1$ and $R^2$ are each independently selected from hydrogen, $C_{1-6}$alkyl, $C_{2-6}$alkenyl, $C_{2-6}$alkynyl, $C_{1-4}$alkoxy, $C_{3-8}$cycloalkyl$C_{1-4}$alkyl, or $(CH_2)_{0-3}R^j$;

$R^j$ is aryl, heteroaryl, $NR^eR^f$ or Het;

Het is a heteroaliphatic ring of 4 to 7 ring atoms, which ring may contain 1, 2 or 3 heteroatoms selected from N, O or S or a group selected from S(O), S(O)$_2$, NH or NC$_{1-4}$alkyl;

$R^e$ and $R^f$ are each independently selected from hydrogen, $C_{1-4}$alkyl or $C(O)C_{1-4}$alkyl;

or $R^e$, $R^f$ and the nitrogen atom to which they are attached form a heteroaliphatic ring of 4 to 7 ring atoms;

and $R^1$ and $R^2$ are optionally substituted by hydroxy, $C_{1-4}$alkyl, =O, $C(O)C_{1-4}$alkyl or $C_{3-8}$cycloalkyl;

or R¹, R² and the nitrogen atom to which they are attached form a heteroaliphatic ring of 4 to 7 ring atoms, which ring optionally contains 1, 2 or 3 additional heteroatoms selected from O or S or a group selected from S(O), S(O)₂, NH or NR$^g$, where R$^g$ is $C_{1-4}$alkyl or heteroaryl, or said heteroaliphatic ring is fused to or substituted by a five- or six-membered nitrogen-containing heteroaliphatic ring, which heteroaliphatic ring is optionally spiro-fused and is optionally substituted by hydroxy, $C_{1-4}$alkyl, $C_{1-4}$alkoxy, $(CH_2)_{0-3}NR^hR^i$, aryl, heteroaryl, or a —CH₂— or —CH₂CH₂— alkylene bridge, where aryl and heteroaryl are optionally substituted by hydroxy, $C_{1-4}$alkyl or $C_{1-4}$alkoxy;

R$^h$ and R$^i$ are each independently selected from hydrogen, $C_{1-4}$alkyl or $C(O)C_{1-4}$alkyl, or R$^h$, R$^i$ and the nitrogen atom to which they are attached form a heteroaliphatic ring of 4 to 7 ring atoms optionally substituted by $C_{1-4}$alkyl; and X is

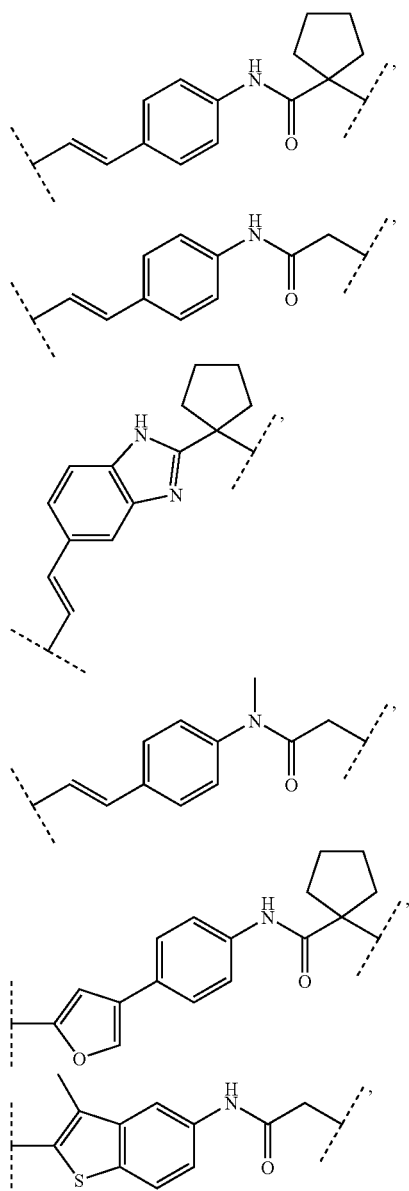

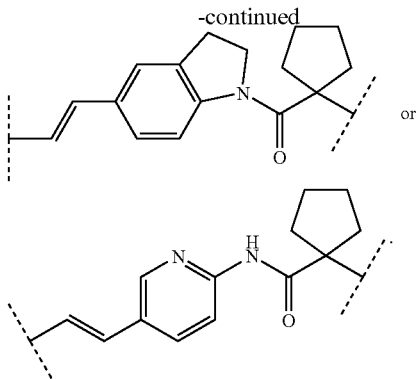

2. A compound as claimed in claim 1, wherein R¹ is hydrogen, $C_{1-6}$alkyl, or $(CH_2)_{0-3}R^j$.

3. A compound as claimed in claim 1, wherein R² is hydrogen, $C_{1-6}$alkyl or $C_{2-6}$alkenyl.

4. A compound as claimed in claim 1, wherein R¹, R² and the nitrogen atom to which they are attached form a five- or six-membered heteroaliphatic ring, which ring optionally contains one additional oxygen atom or a group NR$^g$, which ring is optionally substituted by $(CH_2)_{0-3}NR^hR^i$.

5. A compound according to claim 1 selected from the group consisting of:

(2E)-3-{4-[({1-[({3-cyclohexyl-1-[2-(dimethylamino)-2-oxoethyl]-2-phenyl-1H-indol-6-yl}carbonyl)amino]cyclopentyl}carbonyl)amino]-phenyl}-acrylic acid, (2E)-3-[4-({1-({[3-cyclohexyl-1-[2-(morpholin-4-yl-2-oxoethyl)-2-phenyl-1H-indol-6-yl]carbonyl}amino)cyclopentyl]carbonyl}amino)-phenyl]acrylic acid, (2E)-3-[4-({[1-({[3-cyclohexyl-1-[2-(dimethylamino)-2-oxoethyl]-2-(4-methoxyphenyl)-1H-indol-6-yl]carbonyl}amino)cyclopentyl]carbonyl}amino)phenyl]acrylic acid, (2E)-3-(2-{1-[({3-cyclohexyl-1-[2-(dimethylamino)-2-oxoethyl]-2-phenyl-1H-indol-6-yl}carbonyl)amino]cyclopentyl}-1H-benzimidazol-5-yl)acrylic acid, (2E)-3-[4-({[1-({[3-cyclohexyl-1-(2-{methyl[(1-methylpiperidin-3-yl)methyl]amino}-2-oxoethyl)-2-phenyl-1H-indol-6-yl]carbonyl}amino)cyclopentyl]carbonyl}amino)-phenyl]acrylic acid, (2E)-3-{4-[({1-[({2-(4-chlorophenyl)-3-cyclohexyl-1-[2-(dimethylamino)-2-oxoethyl]-1H-indol-6-yl}carbonyl)amino]cyclopentyl}carbonyl)amino]phenyl}acrylic acid, 5-[({1-[({3-cyclohexyl-1-[2-(dimethylamino)-2-oxoethyl]-2-phenyl-1H-indol-6-yl}carbonyl)amino]cyclopentyl}carbonyl)amino]-3-methyl-1-benzothiophene-2-carboxylic acid, (2E)-3-{4-[[N-({3-cyclohexyl-1-[2-(dimethylamino)-2-oxoethyl]-2-phenyl-1H-indol-6-yl}carbonyl)glycyl](methyl)amino]phenyl}acrylic acid, 4-{4-[({1-[({3-cyclohexyl-1-[2-(dimethylamino)-2-oxoethyl]-2-phenyl-1H-indol-6-yl}carbonyl)amino]cyclopentyl}carbonyl)amino]phenyl}-2-furoic acid, (2E)-3-{4-[({1-[({3-cyclohexyl-1-[2-(4-methylpiperazin-1-yl)-2-oxoethyl]-2-phenyl-1H-indol-6-yl}carbonyl)amino]cyclopentyl}carbonyl)amino]phenyl}acrylic acid, (2E)-3-{4-[({1-[({3-cyclohexyl-1-[2-(glycyl-amino)-2-oxoethyl]-2-phenyl-1H-indol-6-yl}carbonyl)amino]cyclopentyl}carbonyl)amino]phenyl}acrylic acid, (2E)-3-[4-({[1-({[3-cyclohexyl-1-(2-oxo-2-{[(5-oxopyrolidin-2-yl)methyl]amino}ethyl)-2-phenyl-1H-indol-6-yl]carbonyl}amino)cyclopentyl]-carbonyl}amino)phenyl]acrylic acid, (2E)-3-(4-{[(1-{[(3-cyclohexyl-1-{2-[4-(dimethylamino)piperidin-1-yl]-2-oxoethyl}-2-phenyl-1H-indol-6-yl)carbonyl]amino}cyclopentyl)carbonyl]amino}phenyl)acrylic acid, (2E)-3-{4-[({1-[({3-cyclohexyl-1-[2-(methylamino)-2-oxoethyl]-2-phenyl-1H-indol-6-yl}carbonyl)amino]cyclopentyl}carbonyl)amino]phenyl}acrylic acid, (2E)-3-[1-({1-[({3-cyclohexyl-1-[2-(dimethylamino)-2-oxoethyl]-2-phenyl-1H-indol-6-yl}carbonyl)amino]cyclopentyl}carbonyl)-2,3-dihydro-1H-indol-5-yl]acrylic acid, (2E)-3-{4-[({1-[({3-cyclohexyl-1-[2-(1,1-dioxidothiomorpholin-4-yl)-2-oxoethyl]-2-phenyl-1H-indol-6-yl}carbonyl)amino]cyclopentyl}carbonyl)amino]phenyl}acrylic acid, (2E)-3-[4-({[1-({[3-cyclohexyl-1-(2-{2-[(dimethylamino)methyl]morpholin-4-yl}-2-oxoethyl)-2-phenyl-1H-indol-6-yl]carbonyl}amino)cyclopentyl]carbonyl}-amino)phenyl]acrylic acid, (2E)-3-{4-[({1-[({3-cyclopentyl-1-[2-(dimethylamino)-2-oxoethyl]-2-phenyl-1H-indol-6-yl}carbonyl)amino]cyclopentyl}carbonyl)amino]phenyl}acrylic acid, (2E)-3-{4-[({1-[({3-cyclohexyl-1-[2-oxo-2-(3-pyrrolidin-1-ylpiperidin-1-yl)ethyl]-2-phenyl-1H-indol-6-yl}carbonyl)amino]cyclopentyl}carbonyl)amino]phenyl}acrylic acid, (2E)-3-[4-({[1-({[1-(2-{[2-(acetylamino)ethyl]amino}-2-oxoethyl)-3-cyclohexyl-2-phenyl-1H-indol-6-yl]carbonyl}amino)cyclopentyl]carbonyl}amino)phenyl]acrylic acid, (2E)-3-{4-[({1-[({3-cyclohexyl-2-{3-[(dimethylamino)methyl]phenyl}-1-[2-(dimethylamino)-2-oxoethyl]-1H-indol-6-yl}carbonyl)amino]cyclopentyl}carbonyl)amino]phenyl}acrylic acid, and (2E)-3-{6-[({1-[({3-cyclohexyl-1-[2-(dimethylamino)-2-oxoethyl]-2-phenyl-1H-indol-6-yl}carbonyl)amino]cyclopentyl}carbonyl)amino]pyridin-3-yl}acrylic acid, and pharmaceutically acceptable salts thereof.

6. A pharmaceutical composition comprising a compound as claimed in claim 1 or a pharmaceutically acceptable salt thereof in association with a pharmaceutically acceptable carrier.

7. The pharmaceutical composition as claimed in claim 6, which further comprises one or more other agents for the treatment of a viral infections.

8. A method of inhibiting hepatitis C virus polymerase, the method involving administering to a human or animal subject suffering from the condition a therapeutically effective amount of a compound as claimed in claim 1 or a pharmaceutically acceptable salt thereof.

9. A method of preparation of a pharmaceutical composition involving admixing at least one compound as claimed in claim 1, or a pharmaceutically acceptable salt thereof, with one or more pharmaceutically acceptable adjuvants, diluents or carriers and/or with one or more other therapeutically active agents.

* * * * *